(12) United States Patent
Dieterle et al.

(10) Patent No.: US 7,589,046 B2
(45) Date of Patent: *Sep. 15, 2009

(54) THERMAL TREATMENT OF THE PRECURSOR MATERIAL OF A CATALYTICALLY ACTIVE MATERIAL

(75) Inventors: Martin Dieterle, Mannheim (DE); Wolfgang Juergen Poepel, Darmstadt (DE); Silke Berndt, Mannheim (DE); Raimund Felder, Neustadt (DE); Signe Unverricht, Mannheim (DE); Klaus Joachim Mueller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 854 days.

This patent is subject to a terminal disclaimer.

(21) Appl. No.: 10/843,632

(22) Filed: May 12, 2004

(65) Prior Publication Data

US 2004/0245681 A1 Dec. 9, 2004

Related U.S. Application Data

(60) Provisional application No. 60/530,620, filed on Dec. 19, 2003, provisional application No. 60/475,501, filed on Jun. 4, 2003.

(30) Foreign Application Priority Data

Jun. 4, 2003 (DE) ................................. 103 25 487
Dec. 19, 2003 (DE) ................................. 103 60 057

(51) Int. Cl.
*B01J 23/00* (2006.01)

(52) U.S. Cl. ....................... 502/311; 502/312; 502/322; 502/323; 502/353

(58) Field of Classification Search ................. 502/300, 502/311, 312, 322, 323, 353; 266/171, 173, 266/176, 190
See application file for complete search history.

(56) References Cited

U.S. PATENT DOCUMENTS

| | | | | | |
|---|---|---|---|---|---|
| 3,881,861 | A | * | 5/1975 | Ritzmann | 432/106 |
| 3,940,236 | A | * | 2/1976 | Weber et al. | 432/14 |
| 4,105,396 | A | * | 8/1978 | Ritzmann | 432/14 |
| RE29,901 | E | * | 2/1979 | Wada et al. | 502/179 |
| 4,415,752 | A | * | 11/1983 | Decker et al. | 562/534 |
| 4,521,618 | A | * | 6/1985 | Arntz et al. | 562/535 |
| 4,925,823 | A | * | 5/1990 | Krabetz et al. | 502/211 |
| 5,173,468 | A | * | 12/1992 | Boehning et al. | 502/209 |
| 5,364,825 | A | * | 11/1994 | Neumann et al. | 502/311 |
| 5,446,004 | A | * | 8/1995 | Tenten et al. | 502/312 |

(Continued)

FOREIGN PATENT DOCUMENTS

DE 2 161 450 6/1972

(Continued)

*Primary Examiner*—Cam N. Nguyen
(74) *Attorney, Agent, or Firm*—Oblon, Spivak, McClelland, Maier & Neustadt, P.C.

(57) ABSTRACT

In a process for the thermal treatment of the precursor material of a catalytically active material in a rotary tube furnace through which a gas stream flows, at least a proportion of the gas stream flowing through the rotary tube furnace is circulated, and the associated rotary tube furnace apparatus and tube-bundle reactors for the partial gas-phase oxidation of acrolein to acrylic acid are loaded with catalysts whose catalytically active material is obtainable by the process for the thermal treatment.

11 Claims, 10 Drawing Sheets

U.S. PATENT DOCUMENTS

| | | | | |
|---|---|---|---|---|
| 5,521,137 | A * | 5/1996 | Martin et al. | 502/311 |
| 5,569,636 | A * | 10/1996 | Martin et al. | 502/311 |
| 5,583,086 | A * | 12/1996 | Tenten et al. | 502/249 |
| 5,637,546 | A | 6/1997 | Tenten et al. | |
| 5,677,261 | A | 10/1997 | Tenten et al. | |
| 5,686,373 | A | 11/1997 | Tenten et al. | |
| 5,705,684 | A | 1/1998 | Hefner et al. | |
| 5,719,101 | A | 2/1998 | Leman | |
| 5,739,391 | A | 4/1998 | Ruppel et al. | |
| 5,807,531 | A | 9/1998 | Hibst et al. | |
| 5,885,922 | A * | 3/1999 | Hibst et al. | 502/305 |
| 5,910,608 | A | 6/1999 | Tenten et al. | |
| 5,959,143 | A * | 9/1999 | Sugi et al. | 562/534 |
| 6,025,523 | A * | 2/2000 | Hecquet et al. | 562/535 |
| 6,036,880 | A | 3/2000 | Komada et al. | |
| 6,063,728 | A | 5/2000 | Hinago et al. | |
| 6,084,126 | A | 7/2000 | Hibst et al. | |
| 6,124,499 | A * | 9/2000 | Hibst et al. | 562/535 |
| 6,143,916 | A | 11/2000 | Hinago et al. | |
| 6,169,214 | B1 | 1/2001 | Tenten et al. | |
| 6,184,173 | B1 | 2/2001 | Hibst et al. | |
| 6,252,122 | B1 * | 6/2001 | Tenten et al. | 568/475 |
| 6,429,332 | B1 * | 8/2002 | Tanimoto et al. | 562/532 |
| 6,545,177 | B2 * | 4/2003 | Tanimoto et al. | 562/535 |
| 6,563,000 | B1 * | 5/2003 | Yunoki et al. | 562/532 |
| 6,638,890 | B2 * | 10/2003 | Tanimoto et al. | 502/300 |
| 6,736,876 | B1 * | 5/2004 | Shin et al. | 75/379 |
| 6,762,148 | B2 * | 7/2004 | Ohishi et al. | 502/318 |
| 6,780,816 | B2 * | 8/2004 | Tanimoto et al. | 502/300 |
| 6,797,839 | B1 * | 9/2004 | Hibst et al. | 562/532 |
| 6,867,163 | B2 * | 3/2005 | Takezawa et al. | 502/321 |
| 6,881,702 | B2 * | 4/2005 | Arnold et al. | 502/311 |
| 6,921,836 | B1 * | 7/2005 | Hibst et al. | 562/535 |
| 7,022,877 | B2 * | 4/2006 | Dieterle et al. | 562/532 |
| 7,038,082 | B2 * | 5/2006 | Borgmeier et al. | 562/598 |
| 7,091,377 | B2 * | 8/2006 | Borgmeier et al. | 562/598 |
| 7,211,692 | B2 * | 5/2007 | Dieterle et al. | 562/535 |
| 2003/0181761 | A1 | 9/2003 | Unverricht et al. | |
| 2003/0181762 | A1 | 9/2003 | Machhammer et al. | |
| 2004/0077481 | A1 * | 4/2004 | Remke et al. | 501/94 |
| 2004/0249183 | A1 * | 12/2004 | Dieterle et al. | 558/323 |
| 2005/0272952 | A1 * | 12/2005 | Cremer et al. | 562/545 |

FOREIGN PATENT DOCUMENTS

| | | |
|---|---|---|
| DE | 198 35 247 | 2/1999 |
| DE | 198 15 281 | 10/1999 |
| DE | 100 46 928 | 4/2002 |
| DE | 102 11 275 | 9/2003 |
| DE | 102 61 186 | 7/2008 |
| EP | DE 618872 | 9/1935 |
| EP | 0 318 295 | 5/1989 |
| EP | 0 529 853 | 3/1993 |
| EP | 0 608 838 | 8/1994 |
| EP | 0 668 104 | 8/1995 |
| EP | 0 714 700 | 6/1996 |
| EP | 0 731 077 | 9/1996 |
| EP | 0 774 297 | 5/1997 |
| EP | 0 895 809 | 2/1999 |
| EP | DE 198 15 281 A1 | 10/1999 |
| EP | 0 962 253 | 12/1999 |
| EP | 1 090 684 | 4/2001 |
| EP | 1 192 987 | 4/2002 |
| EP | 1 254 709 | 11/2002 |
| EP | 1 260 495 | 11/2002 |
| EP | 1 262 235 | 12/2002 |
| GB | 1 377 637 | 12/1974 |
| WO | WO 95/11081 | 4/1995 |
| WO | WO 01/96270 | 12/2001 |
| WO | WO 02/24620 | 3/2002 |

* cited by examiner

THERMAL TREATMENT OF THE PRECURSOR MATERIAL OF A CATALYTICALLY ACTIVE MATERIAL

BACKGROUND OF THE INVENTION

The present invention relates to a process for the thermal treatment of the precursor material of a catalytically active material in a rotary tube furnace through which a gas stream flows.

In this document, the term catalytically active material is to be understood as meaning solids which are used in chemical reactions, for example in chemical gas-phase reactions, in addition to the reactants, either to reduce the temperature required for carrying out the chemical reaction and/or to increase the selectivity of the formation of the desired product. The chemical reaction takes place as a rule at the surface (interface) of the catalytically active material.

Examples of such heterogeneously catalyzed reactions, which can be carried out in principle both in the liquid phase and in the gas phase, are heterogeneously catalyzed hydrogenations, dehydrogenations and oxydehydrogenations, but also partial oxidations and partial ammoxidations. There, the active material can be used both in powder form and in the form obtained after shaping to give geometric moldings (the latter can be effected, for example, by introduction (absorption) into the inner surface of a premolded support (the term supported catalyst is then used), by application to the outer surface of a premolded support (the term coated catalyst is then used) or by compression (the term unsupported catalysts is then used)). The shaping can be applied to the precursor material itself or only to the catalytically active material.

A complete oxidation of an organic compound (for example a saturated or unsaturated hydrocarbon, an alcohol or an aldehyde) is understood in this document as meaning that all the carbon contained in the organic compound is converted into oxides of carbon ($CO$, $CO_2$).

All other reactions of organic compounds with oxygen (including the oxydehydrogenations) are regarded in this document as partial oxidations. The partial ammoxidation differs from the partial oxidation through the additional presence of ammonia.

It is now generally known that catalytically active materials, molded or unmolded, are generally obtainable by producing a precursor material which as a rule is catalytically inactive or may have reduced activity and may be molded or still unmolded, and exposing said precursor material to a specific gas atmosphere at elevated temperatures.

For example, DE-A 10211275 describes, in its working examples, the activation of a precursor material of a dehydrogenation catalyst at elevated temperature (500° C.) in changing gas streams (hydrogen, air, nitrogen) and its use in catalysts for the heterogeneously catalyzed dehydrogenation of hydrocarbons in the gas phase.

Similarly, EP-A 529853, EP-A 318295, EP-A 608838, WO 01/96270, EP-A 731077, EP-A 1260495, EP-A 1254709, EP-A 1192987, EP-A 962253, EP-A 1262235, EP-A 1090684, DE-A 19835247, EP-A 895809, DE-A 10261186, EP-A 774297, WO 02/24620, EP-A 668104, DE-A 2161450, EP-A 724481, EP-A 714700, DE-A 10046928 and DE-A 19815281 describe the thermal treatment of precursor materials of multielement oxide active materials in a very wide range of gas atmospheres. In these publications, the resulting multielement oxide active materials are recommended and used as catalytic active materials in catalysts for a very wide range of heterogeneously catalyzed partial gas-phase oxidations and gas-phase ammoxidations of organic compounds.

In principle, such thermal treatments can be carried out in a very wide range of furnace types, for example tray furnaces, rotary furnaces, belt calciners, fluidized-bed ovens or shaft furnaces.

Of increasing importance (cf. WO 02/24620) is that all of the precursor material to be thermally treated is treated under very uniform conditions in order to obtain a total amount of active material which has very uniform characteristics.

For example, amounts of active material which have very uniform characteristics are more suitable for heterogeneous gas-phase catalyses with high reactant loading of the active material since they permit particularly uniform thermal reaction conditions over a reactor cross section.

Against this background, WO 02/24620 recommends carrying out the thermal treatment of such precursor materials by means of a special belt calcination apparatus. A disadvantage of a belt calcination, however, is that it is effected on stationary beds of the precursor material. However, temperature gradients which prevent a uniform thermal treatment over the entire precursor material to be thermally treated usually form within such a stationary bed.

A thermal treatment of the precursor material in a moving bed, as is present in thermal treatments in rotary tube furnaces, would be preferable in comparison. Owing to the continuous mobility of the precursor material in rotary tube furnaces, said material forms a continuously self-homogenizing bed, within which, for example, hot spots or cold spots do not form (most thermal treatments of precursor materials involve exothermic or endothermic processes which lead to the formation of hot spots (locations of maximum temperature within the thermally treated precursor material) or to the formation of cold spots (locations of minimum temperature within the thermally treated precursor material)). However, both excessively high and excessively low temperatures adversely affect the catalytic properties of the active material.

Another point of view is that the predominant number of thermal treatments of precursor materials is accompanied by thermal decomposition processes of chemical components contained in the precursor material, with formation of gaseous decomposition products which may have an advantageous or disadvantageous effect on the resulting quality of the active material. In both cases, self-homogenization in a moving bed would be advantageous.

A thermal treatment of precursor material of an active material in a rotary tube furnace is suggested, inter alia, in DE-A 19815281 (e.g. example 1), DE-A 10046928 (e.g. preparation example 1) and EP-A 714700 (working examples).

Surprisingly, such a thermal treatment in a rotary tube furnace is carried out industrially in such a way that the angle of inclination of the rotary tube with the horizontal is adjusted to a value other than zero. The highest point of the rotary tube is the point of introduction of the precursor material and the lowest point is the location of the material discharge. The rotary tube is operated continuously, i.e. the precursor material to be thermally treated is fed continuously to one side of the rotary tube, transported continuously in the rotary tube from the highest to the lowest point and continuously discharged there. Along the way through the rotary tube, the precursor material usually undergoes thermal treatment.

A disadvantage is that such a continuous procedure permits only comparatively short residence times of the material to be thermally treated in the rotary tube.

For establishing the desired gas atmosphere, usually a corresponding gas stream is passed through the rotary tube, countercurrently to the transported precursor material. In the simplest case, said gas stream may consist of air but in other cases, inter alia, also of useful gases (for example reducing gases, such as hydrogen or ammonia, or inert gases, such as nitrogen).

A disadvantage of the procedure described is the comparatively high requirement of such gases, which are not used further after leaving the rotary tube. Another disadvantage is that gases which are formed in the material by thermal decomposition and have a favorable effect are discharged with the gas stream and can no longer display their advantageous effect (e.g. $NH_3$ formed from $NH_4^+$, $NO_2$ formed from $NO_3^-$, or $CO_2$ or CO formed from $CO_3^{2-}$,). Such an advantageous effect may be, for example, a reducing effect.

The temperature desired in the material present in the rotary tube is usually generated indirectly by bringing the rotary tube wall to a certain temperature from the outside.

In order to avoid pronounced radial and axial temperature gradients in the rotary tube, it would be desirable to feed the gas stream passed through the rotary tube into the rotary tube after said gas stream has been preheated to the temperature desired for the material in the rotary tube.

Usually, this heat content of the gas stream would not be used further on leaving the rotary tube, which is a disadvantage.

DETAILED DESCRIPTION OF THE INVENTION

It is an object of the present invention, in view of this prior art, to provide a process for the thermal treatment of the precursor material of a catalytic active material in a rotary tube furnace through which a gas stream flows, which process substantially remedies the disadvantages of the processes of the prior art.

We have found that this object is achieved by a process for the thermal treatment of the precursor material of a catalytic active material in a rotary tube furnace through which a gas stream flows, wherein at least a portion of the gas stream flowing through the rotary tube furnace is circulated.

In the simplest case, the gas stream flowing through the rotary tube furnace may consist of air, but may also contain useful gases, such as CO, $CO_2$, $NH_3$, $N_2$, $NO_x$, $SO_2$ or acetonitrile, or consist of these gases. However, it may also contain a mixture of these gases or consist of such a mixture.

In the novel process, the gas stream flowing through the rotary tube furnace may be from >0 to 500 m³(S.T.P.)/h (or up to 300 m³(S.T.P.)/h in the case of precursor materials in powder form). Frequently, the gas stream flowing through the rotary tube furnace may be from $\geq$50 to 500 (or 300), in general from 100 to 300, m³(S.T.P.)/h.

A suitable rotary tube furnace apparatus is required for carrying out the novel process. The design of such an apparatus is to be described below, without thereby in any way restricting the novel process or the rotary tube furnace apparatuses which can be used for this purpose.

A schematic diagram of this rotary tube furnace apparatus suitable by way of example for the novel process (and used in the working example) is shown in FIG. 1, to which reference numerals used below also relate. Regulation procedures are preferably effected under computer control.

A central element of such a rotary tube furnace apparatus suitable for carrying out the novel process is the rotary tube (1).

It may be, for example, 4 000 mm long and have an internal diameter of 700 mm. It may be produced from stainless steel 1.4893 and have a wall thickness of 10 mm (rotary tube lengths of up to 15 m, frequently of up to 12 m, are of course also suitable for the novel process; as a rule, the rotary tube length in the novel process is $\geq$1 m, as a rule $\geq$4 m; the internal diameter is usually from 20 cm to 2 m, frequently from 20 cm to 1 m).

Reciprocating lances can be mounted in an expedient manner on the inner surface of the rotary tube furnace. It serves primarily for raising the precursor material to be thermally treated in the rotary tube furnace (the material to be thermally treated) and thus promoting the self-homogenization in a moving bed. The height of the reciprocating lances may be 5 cm, based on the other dimensions, stated by way of example, of the rotary tube apparatus described by way of example and suitable according to the invention (all of which dimensions relate to one another and are used in the working example). In principle, an individual reciprocating lance may extend over the entire length of the rotary tube. Expediently, however, a reciprocating lance extends only over a part of the length of the rotary tube. In the exemplary embodiment, they may have, for example, a length of 23.5 cm. In these cases, it is advantageous according to the invention if a plurality (a multiple) of reciprocating lances (e.g. four=a quadruple) are mounted at one and the same height of the rotary tube furnace equidistant over the circumference (e.g. every 90°). It is advantageous in terms of application technology if a plurality of such multiples is present along the rotary tube. In the exemplary embodiment, eight such quadruples (in each case 23.5 cm apart) are present along the rotary tube. The reciprocating lances of two adjacent multiples (quadruples) are present on the circumference of the rotary tube, preferably staggered relative to one another. Advantageously, no reciprocating lances are present at the beginning and at the end of the rotary tube furnace (first and last 23.5 cm in the exemplary embodiment).

The circumferential velocity of the rotary tube can advantageously be varied. Typical speeds are from >0 to 5 or 3 revolutions per minute. The rotary tube is expediently rotatable either counterclockwise or clockwise. For example, in the case of clockwise rotation, the material remains in the rotary tube; for example, in the case of counterclockwise rotation, the precursor material to be thermally treated is transported by the inclination of the rotary tube from the feed (3) to the discharge (4) and removed from the rotary tube by means of a discharge aid (e.g. a paddle).

The angle of inclination of the rotary tube with the horizontal can advantageously be varied. Typical ranges are from 0 to 4° or 2°. In batchwise operation, it is in fact 0°. In continuous operation, the lowest point of the rotary tube is located at the material discharge.

The material feed is expediently volume-controlled via a rotary-vane feeder or is carried out with mass control by means of a balance. The material discharge is, as stated above, controlled via the direction of rotation of the rotary tube.

During batchwise operation of the rotary tube which is dimensioned as above (and could also be dimensioned larger or smaller for carrying out the novel process, as stated above), an amount of from 200 to 600 kg of material can be thermally treated. Said amount is usually present exclusively in the heated part of the rotary tube.

In order, as required according to the invention, to be able to circulate at least a portion of the gas stream flowing through the rotary tube furnace, the rotary tube furnace apparatus to be used according to the invention requires a circulation capacity necessary for this purpose (in the simplest case, a pipeline system). While this is set up statically, the rotary tube is necessarily mounted in a movable manner (rotation).

In order in each case to connect the stationary and the rotating element to one another at the rotary tube entrance and at the rotary tube exit, it is possible to use either ball bearings or gaps which are sealed by graphite or Teflon rings (graphite or Teflon press-fit seals). Owing to their stability to high temperature, graphite press-fit seals are preferred.

Expediently, the rotary tube tapers at its beginning and at its end and projects into that tube of the circulation pipe which leads in and leads out, respectively.

These connections are advantageously flushed with sealing gas. The two flushing streams (11) supplement the gas stream passed through the rotary tube, at the entrance of the gas stream into the rotary tube and at the exit of the gas stream from the rotary tube. The chemical composition of the flushing streams can be adapted to the temperature desired in the rotary tube for the thermal treatment. For example, air can be used as the sealing gas. Particularly in the case of thermal treatments carried out at relatively high temperatures, however, inert gas (e.g. nitrogen) is preferably used as sealing gas since this in fact simultaneously results in protection from oxidation in addition to producing the sealing effect. The amount of sealing gas is preferably kept low. An individual flushing stream of this type is therefore expediently from >0 to 50, preferably from 1 to 50, $m^3$(S.T.P.)/h.

The sealing effect is important, inter alia, for preventing any of the gas atmosphere which prevails in the rotary tube itself and frequently also contains components which are not completely toxicologically safe (e.g. $CO_2$, $NO_x$, $NH_3$, CO, $SO_2$, acetonitrile) from entering the surrounding atmosphere through static/rotating connections.

The recycle gas stream (gas circulation) is transported by means of a recycle gas compressor (13) (fan, e.g. a fan of the type KXE 160-004030-00, from Konrad Reitz GmbH), which aspirates in the direction of the gas stream flowing out of the rotary tube and applies pressure in the other direction. Immediately downstream of the cycle gas compressor, the gas pressure is as a rule above atmospheric pressure (i.e. above one atmosphere). A recycle gas outlet (recycle gas can be discharged via a control valve (14) and is aspirated via the exit gas compressor (17) (fan; e.g. of the type T100/315-R3/500, from Meidinger)) is located downstream of the recycle gas compressor. It is expedient according to the invention if a pressure reducer (15), e.g. an aperture plate (cross-sectional constriction; e.g. by about a factor of 3) is present downstream of the outlet point for the recycle gas. Said pressure reducer provides a simple possibility for aspirating more gas on the intake side of the recycle gas compressor than is delivered on the pressure side of the recycle gas compressor.

In this way, a slightly reduced pressure can be established in the rotary tube, i.e. the pressure of the gas stream flowing through the rotary tube may be below the ambient pressure of the rotary tube on leaving the rotary tube. This measure additionally helps to ensure that none of the gas atmosphere in the rotary tube escapes to the outside. In the rotary tube, it is however also possible to establish slightly superatmospheric pressure relative to the ambient pressure. Frequently, the pressure directly downstream of the exit of the gas stream from the rotary tube is brought to a value in the range from +1.0 above to −1.2 mbar below the external pressure, i.e. the pressure of the gas stream flowing through the rotary tube may be below the ambient pressure of the rotary tube on leaving the rotary tube. This is preferred according to the invention.

The pressure in the rotary tube is expediently established on the basis of pressure measurements by means of a pressure sensor. Suitable pressure sensors are, for example, those of the type AMD 220, from Hartmann & Braun, which operate according to the pressure transducer (membrane measuring unit) principle. It is expedient in terms of application technology if the pressure sensor (16) is positioned directly downstream of the exit of the gas stream from the rotary tube. A further pressure sensor may be present upstream of the entrance of the gas stream into the rotary tube. This may also be a single pressure sensor. The pressure can then be established through the cooperation of pressure sensor (16), exit gas compressor (17) (fan which aspirates in the direction of the control valve), recycle gas compressor and fresh gas feed. If the two compressors and the fresh gas feed operate in a steady state (or if noncontrollable compressors are used), the control valve (14) is the sole pressure adjusting screw.

The velocity of the gas stream transported through the rotary tube is typically ≧0.1 m/s and ≦2 m/s.

According to the invention, the material in the rotary tube is expediently heated by heating the rotary tube from outside. In principle, this heating can be effected by direct firing, i.e. burners whose hot combustion gases are transported around the rotary tube surrounded by an envelope, for example with the aid of fans, are mounted below the rotary tube.

Preferably, however, the rotary tube is surrounded by an envelope, e.g. a right parallelepiped, which has electrically heated elements on its inside (resistance heating). For reasons relating to temperature homogeneity, the envelope should have such heating elements at least on two opposite sides. Preferably, however, the heating elements surround the rotary tube on all sides. Their distance from the outer surface of the rotary tube is typically from 10 to 20 cm. In the embodiment described here by way of example (FIG. 1), the rotary tube rotates freely in a right parallelepiped (2) which has four equally long, electrically heated (resistance heating) heating zones in succession along the length of the rotary tube, each of which heating zone encloses the circumference of the rotary tube furnace. Each of the heating zones can heat the corresponding rotary tube section to temperatures from room temperature to 850° C. The maximum heating power of each heating zone is 30 kW. The distance between electrical heating zone and outer surface of the rotary tube is about 10 cm. At the beginning and at the end, the rotary tube projects about 30 cm out of the right parallelepiped.

In addition, a heater (10) offers the possibility of heating the gas stream passed into the rotary tube to the desired temperature before its entry into the rotary tube (e.g. to the temperature desired for the material in the rotary tube), in order thus to support the thermostating of the material present in the rotary tube furnace. If the thermal treatment of the precursor material is accompanied by an exothermic chemical reaction in the precursor material, the gas stream passed into the rotary tube is, according to the invention, advantageously fed into the rotary tube at a temperature which is below the temperature (e.g. up to 50° C., frequently up to 20° C.) which is intended for the material in the rotary tube furnace. If, on the other hand, the thermal treatment of the precursor material is accompanied by an endothermic chemical reaction in the precursor material, the gas stream passed into the rotary tube is, according to the invention, advantageously passed into the rotary tube at a temperature which is above the temperature (e.g. up to 50° C., frequently up to 20° C.) which is intended for the material in the rotary tube furnace.

In principle, the heater (10) may be a heater of any kind. For example, it may be an indirect heat exchanger. Such a heater can in principle also be used as a condenser (by adapting the temperature of the heating medium, e.g. use of cooling brine). The heater can in principle also be heated by means of direct or indirect firing. Direct or indirect steam heating is also suitable. In the case of direct steam heating, the recycle gas pipe is expediently at least partly trace-heated in order to suppress undesired condensation of the steam contained in the gas stream or, if required, specifically to separate off the steam by condensation. An electrical heater in which the gas stream is passed over electrically heated (resistance heating) metal wires is frequently employed. In the embodiment described by way of example, a CSN continuous flow heater, type 97 D 80 from Schniewindt KG, 58805 Neuerade, Germany, whose maximum power is 1×50 kW+1×30 kW, is employed.

Both the heating of the rotary tube furnace and the heating of the gas stream passed into the rotary tube are expediently controlled via the temperature of the material in the rotary tube. This is determined, as a rule, by means of a thermocouple projecting into the material. In the embodiment described by way of example, a lance (8), from which altogether three thermocouples (9) lead vertically into the material at intervals of 800 mm, is located for this purpose on the central axis of the rotary tube. The arithmetic mean of the three thermocouple temperatures is then understood as the temperature of the material. Inside the material present in the rotary tube, the maximum deviation of two measured temperatures is expediently, according to the invention, less than 30° C., preferably less than 20° C., particularly preferably less then 10° C., very particularly preferably less than 5 or 3° C.

In the novel process, the thermal treatment is frequently carried out at from 100 to 1 100° C. or from 200 to 800° C. This applies in particular where the catalytically active material is a multielement oxide material, e.g. a multimetal oxide material.

In the case of a multielement oxide material as catalytically active material, the novel process is particularly preferably carried out either at from 600 to 800° C. or at from 300 to 600° C. (abovementioned temperatures are always the material temperature).

Very generally, as a rule a catalytically active material is obtained as the result of the novel process.

The temperature rate at which the precursor material present in the rotary tube is heated up for the purpose of its thermal treatment is usually $\leqq 10°$ C./min in the novel process. Frequently, the temperature rate is $\leqq 8°$ C./min, often $\leqq 5°$ C./min or $\leqq 3°$ C./min, and it is often $\leqq 2°$ C./min or $\leqq 1°$ C./min. As a rule, however, this temperature rate is $\geqq 0.1°$ C./min, in general $\geqq 0.2°$ C./min, frequently $\geqq 0.3°$ C./min or $\geqq 0.4°$ C./min.

As stated above, the thermal treatment of the precursor material of a catalytically active material is frequently accompanied by an exothermic chemical reaction in which components of the gas stream passed through the rotary tube are also frequently involved.

For the novel process, it is important that this chemical reaction does not take place in an uncontrolled manner and the heat liberated by the chemical reaction is removed rapidly, since an uncontrolled course can lead to excessive heat generation and uncontrolled temperature increase of the thermally treated material, which finally results in a deterioration in the properties of the active material.

In order, if necessary, to be able to counteract in good time such an uncontrolled course of the thermal treatment of the material, a rotary tube apparatus suitable for the novel process advantageously has a means for rapid cooling. This can be effected, for example, in a particularly efficient manner if the envelope surrounding the rotary tube (the right parallelepiped in the exemplary embodiment) has, on one side (e.g. in the lower part) orifices (longest dimension typically 60 cm) or holes through which ambient air or previously cooled air can be aspirated by means of a fan (5) (e.g. one of the type E 315/40-63, from Ventapp GmbH) and can be discharged through flaps (7) present on the other (opposite) side (e.g. in the upper part) of the envelope and having an adjustable orifice. The rotary tube heating is frequently simultaneously switched off. Such rapid cooling also makes it possible to terminate the thermal treatment at exactly the right time and thus to prevent excessive thermal treatment. As an additional measure, the gas stream can be cooled (in the heater (10)) before being fed into the rotary tube.

The rapid cooling makes it possible, for example at the end of the thermal treatment of the precursor material, to reduce the temperature of the material present in the rotary tube within a period of $\leqq 5$, in general $\leqq 4$, frequently $\leqq 2$, hours by at least 300° C. As a rule, however, this cooling period is not less than 0.5 hour.

It is expedient in terms of application technology if fresh gas is metered into the actually recirculated recycle gas fraction (19) between the pressure reducer (15) and the heater (10). As in the exemplary embodiment shown in FIG. 1, a fresh gas base load (e.g. nitrogen (20)) is frequently metered in. By means of at least one splitter, it is then possible to respond to the measured values of the various component sensors used and to regulate in detail the component contents of the gas stream fed into the rotary tube. In the exemplary embodiment, this is a nitrogen/air splitter (21) which responds to the measured value of the oxygen sensor.

The component sensors are expediently installed (18) upstream of the recycle gas compressor. However, they could also be installed at another point.

By means of these sensors, reducing gas components, such as $NH_3$, $CO$, $NO$, $N_2O$, acetic acid or aerosols (e.g. ammonium acetate) and oxidizing components, such as $NO_2$ and $O_2$, are frequently determined, the content of which must often be within particularly narrow limits.

In the exemplary embodiment, two sensors (18) are installed, i.e. one for determining the ammonia content and one for determining the oxygen content. The ammonia sensor generally preferably operates according to an optical measuring principle (the absorption of light of certain wavelengths is proportional to the ammonia content of the gas). In the exemplary embodiment it is an apparatus from Perkin & Elmer of the type MCS 100. On the other hand, oxygen sensors are based as a rule on the paramagnetic properties of oxygen. In the exemplary embodiment, an Oximat from Siemens of the type Oxymat MAT SF 7MB 1010-2CA01-1AA1-Z is expediently used as the oxygen sensor.

In the case of catalytic multimetal oxide active materials, oxygen absorption from the gas atmosphere prevailing in the rotary tube frequently takes place during the transition from the precursor material to the catalytically active material in the course of the novel thermal treatment. By means of oxygen sensors installed upstream of the entrance of the gas stream into the rotary tube and downstream of the exit of the gas stream from the rotary tube, this oxygen absorption can be quantitatively detected online and the oxygen supply in the gas stream flowing through the rotary tube can be correspondingly adapted (if such an adaptation is not effected, the oxygen supply in the gas stream fed to the rotary tube is usually kept substantially constant). Over- or underoxidations of the active material can thus be avoided and hence the catalyst performance improved. It is also possible to proceed entirely analogously with reducing gas components.

The novel recycle gas procedure also proves to be particularly advantageous in this context when the character of the gas atmosphere prevailing in the rotary tube is changed from reducing to oxidizing or vice versa in the course of the thermal treatment. Such a procedure does in fact make it possible to carry out this change in a simple manner so that the gas atmosphere in the rotary tube is always outside the explosion range.

In tests of the novel process, it has frequently been found that the gas component sensors have indicated incorrect values.

Very accurate investigations of this situation have shown that this is due to the fact that the gas stream flowing through the rotary tube generally also discharges very fine dust which originates from the precursor material to be thermally treated and is deposited on the sensor surface (the sensors operate as a rule in such a way that they aspirate portions from the gas stream) and falsifies the measurements. Only using filters installed upstream of the sensors could not remedy this problem since they become blocked as a function of time and thus also falsify the results of the measurement.

A suitable solution to the problem is a cyclone (12) installed downstream of the outlet (but upstream of the sensors) of the gas stream passed through the rotary tube, for separating off solid particles entrained by the gas stream (the centrifugal separator separates solid particles suspended in the gas phase by cooperation of centrifugal and gravitational force; the centrifugal force of the gas stream rotating in the form of a vortex accelerates the sedimentation of the suspended particles).

The concomitant use of such a cyclone also prevents the very fine dust from being deposited on the walls of the recycle gas pipe (such deposition of very fine dust would have a noticeable disadvantageous effect, for example in the case of a product change; i.e. if the precursor material to be thermally treated is changed, the subsequent material may be contaminated, in the course of a passage of recycle gas, with the previously treated precursor material dust deposited on the walls; furthermore, the very fine dust may damage (change of heat transfer) or block the heater (10)).

The solid deposited in the cyclone is disposed of.

The pressure drop produced by the cyclone is compensated by the recycle gas compressor.

Instead of a cyclone, it is also possible in principle to use any other apparatus which is suitable for separating finely divided solids from a gaseous dispersion phase.

The discharged recycle gas fraction (22) (exit gas) frequently contains gases, such as $NO_x$, CO, acetic acid, $NH_3$, etc., which are not completely safe, and it is for this reason that said gases are usually separated off in an exit gas purification apparatus (23).

For this purpose, the exit gas is generally first passed via a scrubber column (this is substantially a column which is free of internals and contains, before its exit, a packing having separation activity); the exit gas and aqueous spray mist are passed cocurrently or countercurrently (2 spray nozzles having opposite spray directions).

Arriving from the scrubber column, the exit gas is expediently fed into an apparatus which contains a fine dust filter (as a rule a bundle of tube filters) from the interior of which the penetrated exit gas is removed. Advantageously, incineration is then finally effected in a muffle furnace.

In the novel process, the principle of mass flow measurement based on Coriolis forces, the principle of aperture plate measurement based on pressure differences and the principle of thermal convection are particularly suitable for regulating the total amount of the gas stream fed through the rotary tube, other than the sealing gas.

In the exemplary embodiment, the measurement of the amount of the gas stream fed to the rotary tube, other than the sealing gas, is effected by means of a sensor (28) from KURZ Instruments, Inc., Montery (USA) of the type Model 455 Jr (measuring principle: mass flow measurement based on thermal convection and using an equal-temperature anemometer).

The rotary tube furnace apparatus described can be operated both continuously and batchwise. According to the invention, it is preferably operated batchwise. The material and gas phase are preferably fed countercurrently through the rotary tube furnace in continuous operation. For example, the multimetal oxide materials of DE-A 19855913 or WO 02/24620 and the preformed phases required for their preparation (e.g. the bismuth tungstates and the bismuth molybdates) are obtainable in an excellent manner by continuous thermal treatment of the precursor material in the rotary tube furnace.

Accordingly, rotary tube furnace apparatuses which comprise:

a) at least one recycle gas compressor (13);

b) at least one exit gas compressor (17);

c) at least one pressure reducer (15);

d) at least one fresh gas feed ((20), (21));

e) at least one heatable rotary tube (1); and f) at least one recycle gas pipe are especially suitable for carrying out the novel process.

If compressors (13) and (17) which are not regulatable are used, the rotary tube furnace apparatus also comprises at least one control valve (14).

Embodiments advantageous according to the invention moreover comprise at least one heater (10).

Very particularly preferred embodiments additionally comprise at least one integrated cyclone.

In addition, it is advantageous if the rotary tube furnace apparatus comprises an apparatus for rapid cooling.

If it is intended to use the rotary tube furnace apparatus also for the thermal treatments of material in which the gas stream passed through the rotary tube is also not at least proportionately circulated, it is expedient if the connection between cyclone (12) and recycle gas compressor (13) can be made according to three-way valve principle (26) and the gas stream can be fed directly into the exit gas purification apparatus (23). In this case, the connection to the exit gas purification apparatus, which connection is located downstream of the recycle gas compressor, is also made according to the three-way valve principle. If the gas stream substantially comprises air, this is aspirated (27) in this case via the recycle gas compressor (13). The connection to the cyclone is likewise made according to the three-way valve principle. In this way, the gas stream is preferably sucked through the rotary tube so that the internal pressure of the rotary tube is less than the ambient pressure.

Preferably, the above treatment is carried out continuously and with countercurrent flow of material and gas stream, i.e. the material to be thermally treated is introduced into the rotary tube furnace at the opposite end to the gas stream (at the highest point of the rotary tube) and discharged from the rotary tube furnace at the opposite end to the gas stream.

In the exemplary embodiment of the rotary tube apparatus, the pressure downstream of the rotary tube exit (of the gas stream) is advantageously set to be −0.8 mbar below the external pressure during continuous operation. During batchwise operation, the same pressure setting is −0.2 mbar.

As stated above, the novel process is suitable for the thermal treatment of precursor materials of catalytically active materials of all types. The precursor material may be subjected to the novel thermal treatment either in powder form or in the form of special (catalyst) moldings.

For example, it is suitable for the preparation of catalytically active multielement oxide materials which contain at least one of the elements Nb and W and the elements Mo and V, the molar fraction of the element Mo, based on the total amount of all elements other than oxygen in the catalytically active multielement oxide material, being from 20 to 80 mol %, the molar ratio of Mo contained in the catalytically active multielement oxide material to V, Mo/V, contained in the catalytically active multielement oxide material being from 15:1 to 1:1, and the corresponding molar ratio Mo/(total amount of W and Nb) being from 80:1 to 1:4. Frequently, such multielement oxide materials also contain Cu in the corresponding molar Mo/Cu ratio of from 30:1 to 1:3. The temperature range of the thermal treatment of the precursor material is typically from 300 to 600° C. The various advantages of the novel process are to be illustrated again below with reference to examples of such multielement oxide materials. They are obtainable, for example, by preparing an intimate dry blend (the precursor material) also containing ammonium ions from starting compounds which contain as components the elemental constituents of the multielement oxide material other than oxygen, and subjecting said dry blend to a thermal treatment at from 300 to 450° C. (material temperature) in an $O_2$- and $NH_3$-containing gas atmosphere. According to EP-B 72448, the gas atmosphere in which the thermal treatment is to be effected is, for example, one which contains from 0.5 to 4% by volume of $O_2$ at every point in time during the thermal treatment,
from 1 to 8% by volume of $NH_3$, averaged over the total duration of the reductive thermal treatment, and
steam and/or inert gas as residual amounts, the $NH_3$ content of the atmosphere during the thermal treatment passing through a maximum which is below 20% by volume.

Abovementioned multielement oxide materials may additionally contain, for example, the elements Ta, Cr, Ce, Ni, Co, Fe, Mn, Zn, Sb, Bi, alkali metals (Li, Na, K, Rb, Cs), H, alkaline earth metals (Mg, Ca, Sr, Ba), Si, Al, Ti and Zr in addition to the elements Nb and/or W, and Mo, V and, if required, Cu. Of course, the multielement oxide material can, however, also consist only of the elements Nb and/or W and Mo, V and, if required, Cu. They are particularly suitable as active materials for catalysts for the heterogeneously catalyzed partial gas-phase oxidation of acrolein to acrylic acid.

Catalytically active multielement oxide materials particularly suitable as active materials for catalysts for the heterogeneously catalyzed partial gas-phase oxidation of acrolein to acrylic acid comply with the following general stoichiometry I

$$Mo_{12}V_aX^1_bX^2_cX^3_dX^4_eX^5_fX^6_gO_n \quad (I)$$

where
$X^1$ is W, Nb, Ta, Cr and/or Ce,
$X^2$ is Cu, Ni, Co, Fe, Mn and/or Zn,
$X^3$ is Sb and/or Bi,
$X^4$ is one or more alkali metals (Li, Na, K, Rb, Cs) and/or H,
$X^5$ is one or more alkaline earth metals (Mg, Ca, Sr, Ba),
$X^6$ is Si, Al, Ti and/or Zr,
a is from 1 to 6,
b is from 0.2 to 4,
c is from 0 to 18, preferably from 0.5 to 18,
d is from 0 to 40,
e is from 0 to 2,
f is from 0 to 4,
g is from 0 to 40 and
n is a number which is determined by the valency and frequency of the elements other than oxygen in I, and where the variables are to be selected within the specified ranges with the proviso that the molar fraction of the element Mo, based on the total amount of all elements other than oxygen in the multielement oxide material (I), is from 20 to 80 mol %, the molar ratio of Mo contained in the catalytically active multielement oxide material (I) to V, Mo/V, contained in the catalytically active multielement oxide material (I) is from 15:1 to 1:1, and the corresponding molar ratio Mo/(total amount of W and Nb) is from 80:1 to 1:4 (and the corresponding molar ratio Mo/Cu is from 30:1 to 1:3, if the multielement oxide material contains Cu).

Preferred among the active multielement oxide materials (I) in turn are those in which
$X^1$ is W, Nb and/or Cr,
$X^2$ is Cu, Ni, Co and/or Fe,
$X^3$ is Sb,
$X^4$ is Na and/or K,
$X^5$ is Ca, Sr and/or Ba,
$X^6$ is Si, Al and/or Ti,
a is from 2.5 to 5,
b is from 0.5 to 2,
c is from 0.5 to 3,
d is from 0 to 2,
e is from 0 to 0.2,
f is from 0 to 1,
g is from 0 to 15 and
n is a number which is determined by the valency and frequency of the elements other than oxygen in I.

However, the following multielement oxide active materials II are very particularly preferably direct products of the novel process:

$$Mo_{12}V_aX^1_bX^2_cX^5_fX^6_gO_n \quad (II),$$

where
$X^1$ is W and/or Nb,
$X^2$ is Cu and/or Ni,
$X^5$ is Co and/or Sr,
$X^6$ is Si and/or Al,
a is from 3 to 4.5,
b is from 1 to 1.5,
c is from 0.75 to 2.5,
f is from 0 to 0.5,
g is from 0 to 8 and
n is a number which is determined by the valency and frequency of the elements other than oxygen in II, and where the variables are to be selected within the specified ranges with the proviso that the molar fraction of the element Mo, based on the total amount of all elements other than oxygen in the multielement oxide active material (II), is from 20 to 80 mol %, the molar ratio of Mo contained in the catalytically active multielement oxide material (II) to V, Mo/V contained in the catalytically active multielement oxide material (II) is from 15:1 to 1:1, the corresponding molar ratio Mo/Cu is from 30:1 to 1:3 and the corresponding molar ratio Mo/(total amount of W and Nb) is from 80:1 to 1:4.

Known suitable sources (starting compounds) of the elemental constituents other than oxygen of the desired multielement oxide active material, in the respective stoichiometric ratio desired in the multielement oxide active material, are used as starting materials for the preparation of such multielement oxide materials, as already mentioned, and a very intimate thermal, preferably finely divided, dry blend is produced from said sources and is then subjected to the thermal treatment, it being possible to carry out said intimate thermal treatment before or after the shaping to (catalyst) moldings of a certain geometry. According to the invention, said thermal treatment is advantageously effected beforehand. The sources may be either already oxides or those compounds which can be converted into oxides by heating, at least in the presence of oxygen. In addition to the oxides, particularly suitable starting compounds are therefore halides, nitrates, formates, oxalates, acetates, carbonates or hydroxides.

Suitable starting compounds of Mo, V, W and Nb are also the oxo compounds thereof (molybdates, vanadates, tungstates and niobates) or the acids derived therefrom. Oxygen-containing sources are likewise advantageous.

The required content of ammonium ions in the intimate dry blend can be realized in a simple manner by incorporating a corresponding amount of ammonium ions into the intimate dry blend. Expediently, the ammonium ions can be introduced into the intimate dry blend, for example, by using the corresponding ammonium oxometallates as sources of the elements Mo, V, W or Nb. Examples of these are ammonium metaniobate, ammonium metavanadate, ammonium heptamolybdate tetrahydrate and ammonium paratungstate heptahydrate. However, independently of the starting compounds required as sources of the multielement oxide active material constituents, ammonium donors, such as $NH_4NO_3$, or $NH_4Cl$, or ammonium acetate, or ammonium carbonate, or ammonium bicarbonate, or $NH_4OH$, or $NH_4CHO_2$, or ammonium oxalate, can of course also be incorporated into the intimate dry blend to be thermally treated.

The thorough mixing of the starting compounds can be carried out in principle in dry or wet form. If it is effected in dry form, the starting compounds are expediently used in the form of finely divided powders and, after the mixing, for example, are compressed (e.g. tableted) to give (catalyst) moldings of the desired geometry, which are then subjected to the novel thermal treatment.

However, the thorough mixing is preferably effected in wet form. Usually, the starting compounds are mixed with one another in the form of an aqueous solution and/or suspension. Particularly intimate dry blends are obtained in the mixing method described when exclusively sources and starting compounds present in dissolved form are used as starting materials. A preferably used solvent is water. The aqueous material (solution or suspension) is then dried and the intimate dry blend thus obtained is, if required, directly subjected to the thermal treatment. The drying process is preferably carried out by spray-drying (the outlet temperatures are as a rule from 100 to 150° C.) and immediately after the preparation of the aqueous solution or suspension. The resulting powder can be molded directly by compression. Frequently, however, it proves to be too finely divided for direct further processing and is then therefore expediently kneaded with addition of, for example, water. The addition of a lower organic carboxylic acid (e.g. acetic acid) often proves advantageous during the kneading (typical added amounts are from 5 to 10% by weight, based on powder material used).

The resulting kneaded material is then either shaped to give the desired geometry, dried and then subjected to thermal treatment (leads to unsupported catalysts) or is only shaped to give extrudates, which are subjected to the thermal treatment and then milled to a powder (usually <80 μm), which, with addition of a small amount of water and, optionally, further conventional binders, is usually applied as a moist material to inert supports. After coating is complete, drying is effected again and a ready-to-use coated catalyst is thus obtained. If the thorough mixing of the starting compounds is effected in the form of a solution, for example an aqueous one, it is also possible for inert porous supports to be impregnated with said solution, dried and then subjected according to the invention to the thermal treatment to give supported catalysts. In the preparation of coated catalysts, the coating of the supports can also be effected before the thermal treatment, for example with the moist spray-dried powder.

Support materials suitable for coated catalysts are, for example, porous or nonporous aluminas, silica, thorium dioxide, zirconium dioxide, silicon carbide or silicates, such as magnesium silicate or aluminum silicate (e.g. steatite of the type C 220 from CeramTec).

The supports may have a regular or irregular shape, supports having a regular shape and pronounced surface roughness, e.g. spheres or hollow cylinders having a chip coating, being preferred.

The use of substantially nonporous spherical steatite supports having a rough surface (e.g. steatite of the type C 220 from CeramTec), whose diameter is from 1 to 8 mm, preferably from 4 to 5 mm, is suitable. However, the use of cylinders whose length is from 2 to 10 mm and whose external diameter is from 4 to 10 mm as supports is also suitable. In the case of annular supports, the wall thickness is moreover usually from 1 to 4 mm. Annular supports preferably to be used have a length of from 2 to 6 mm, an external diameter of from 4 to 8 mm and a wall thickness of from 1 to 2 mm. Rings measuring 7 mm×3 mm×4 mm (external diameter×length×internal diameter) are also particularly suitable as supports.

The coating of the supports with finely divided multielement oxide active material obtainable in the manner described by thermal treatment, or with the finely divided precursor material thereof still to be subjected to the thermal treatment (intimate dry blend), is carried out as a rule in a rotatable container, as disclosed, for example, in DE-A 2909671, EP-A 293859 or in EP-A 714700. The procedure of EP-A 714700 is preferred.

Expediently, for coating of the supports, the support is moistened with the powder material to be applied. After the application, drying is usually effected by means of hot air. The coat thickness of the powder material applied to the support is expediently chosen to be in the range from 10 to 1000 μm, preferably from 50 to 500 μm, particularly preferably from 150 to 250 μm.

In the case of unsupported catalysts, the shaping can, as stated above, also be effected before or after the thermal treatment is carried out.

For example, unsupported catalysts can be prepared from the powder form of the multielement oxide active material obtainable according to the invention or its precursor material still to be subjected to the thermal treatment (the intimate dry blend), by compaction to give the desired catalyst geometry (e.g. by tableting or extrusion), it being possible, if required, to add assistants, e.g. graphite or stearic acid as lubricants and/or molding assistants and reinforcing agents, such as microfibers of glass, asbestos, silicon carbide or potassium titanate. Suitable geometries for unsupported catalysts are, for example, solid cylinders or hollow cylinders having an external diameter and a length of from 2 to 10 mm. In the case of the hollow cylinders, a wall thickness of from 1 to 3 mm is expedient. Of course, the unsupported catalyst may also have spherical geometry, it being possible for the sphere diameter to be from 2 to 10 mm.

The relevant multielement oxide active materials can of course also be used in powder form, i.e. without shaping to give specific catalyst geometries, as catalysts for the heterogeneously catalyzed partial oxidation of acrolein to acrylic acid (e.g. also in a fluidized bed).

The partial gas-phase oxidation of acrolein to acrylic acid itself can be carried out using the multielement oxide active materials described, for example as described in EP-A 724481 or as described in DE-A 19910508.

Regarding the thermal treatment of the precursor materials of the multielement oxide materials described above, EP-B 724481 states (page 5, line 25 et seq.):

"The calcination atmosphere required according to the invention can be realized in a simple manner, for example, by carrying out calcination in an oven through which a gas mixture which has the corresponding composition with regard to $O_2$, $NH_3$ and inert gases/steam is passed. In a less preferable embodiment, the required average ammonia content of the calcination atmosphere may also be achieved by incorporating a corresponding amount of ammonium ions into the dry material to be calcined, said ions decomposing in the course of the calcination with evolution of $NH_3$."

The calcination in EP-B 724481 was carried out in through-circulation ovens, inter alia a gas mixture which contained a certain proportion by volume of $NH_3$ (% by volume) being fed to said ovens.

By means of the invention on which this application is based, the less preferable embodiment of EP-B 724481 now becomes a preferred embodiment. This is due, inter alia, to the fact that the novel process no longer requires an external addition of $NH_3$ to the calcination atmosphere but, through the passage of recycle gas, manages with the ammonium ions contained in the precursor material to be thermally treated, as an ammonia source. As a further advantage, through the passage of recycle gas, the process of the present patent application reduces the energy requirement for the thermal treatment by further utilizing the energy content contained in the recycle gas. In addition, owing to the continuously self-homogenizing bed in the rotary tube, the novel process permits the preparation of large amounts of catalytically active materials (in particular catalytically active multielement oxide materials) having a particularly narrow activity distribution within the prepared batch. This is particularly important in the case of said catalytically active multielement oxide materials which contain at least one of the elements Nb and W and the elements Mo, V and Cu and which are to be used for the preparation of catalysts for the heterogeneously catalyzed partial gas-phase oxidation of acrolein to acrylic acid, especially when this gas-phase partial oxidation is carried out at high acrolein loads, as described, for example in DE-A 10307983, DE-A 19948523 and DE-A 19910508.

As a rule, this gas-phase partial oxidation of acrolein is in fact carried out in a tube-bundle reactor having one or more temperature zones, as described, for example, in EP-A 700714, EP-A 700 893, DE-A 19910508, DE-A 19948523, DE-A 19910506, DE-A 19948241, DE-C 2830765, DE-C-2513405, U.S. Pat. No. 3,147,084, DE-A 2201528, EP-A 383224 and DE-A 2903218.

The solid catalyst bed is present in the metal tubes (catalysts) of the tube-bundle reactor and the heating medium or media is or are passed around the metal tubes (in the case of more than one temperature zone, a corresponding number of spatially separated heating media are passed around the metal tubes). The heating medium is as a rule a salt melt. The reaction mixture is passed through the catalyst tubes.

The catalyst tubes are usually produced from ferritic steel and typically have a wall thickness of 1 to 3 mm. Their internal diameter is as a rule from 20 to 30 mm, frequently from 21 to 26 mm. Their length is expediently from 2 to 4 m.

It is expedient in terms of application technology that the number of catalyst tubes housed in the tube-bundle container is at least 5000, preferably at least 10 000. Frequently, the number of catalyst tubes housed in the reactor container is from 15 000 to 30 000. Tube-bundle reactors having more than 40 000 catalyst tubes tend to be the exception. Within the container, the catalyst tubes are usually homogeneously distributed (preferably 6 equidistant neighboring tubes per catalyst tube), the distribution expediently being chosen so that the distance between the central internal axes of adjacent catalyst tubes (i.e. the catalyst tube spacing) is from 35 to 45 mm (cf. for example EP-B 468290).

The use of melts of salts such as potassium nitrate, potassium nitrite, sodium nitrite and/or sodium nitrate or of metals having a low melting point, such as sodium, mercury and alloys of various metals, is particularly advantageous as the heat exchange medium.

Although it is generally possible, by suitable flow conditions in the tube-bundle reactors, to ensure that the same salt bath temperature acts over each individual catalyst tube, considered over the reactor section, the presence of temperature gradients over the reactor cross section cannot be completely avoided in practice. If the temperature gradients over the reactor cross section are additionally accompanied by pronounced activity gradients over the individual catalyst tube loads, this may adversely affect the safety of operation of the tube-bundle reactor since the heat generation due to the exothermic heterogeneously catalyzed fixed-bed partial oxidation of acrolein to acrylic acid in the individual catalyst tubes of a tube-bundle reactor would be significantly different in such a case. The latter would occur because an increased activity of the catalyst tube load means that there is a higher conversion and hence more heat is generated at the same temperature per unit time.

The novel process permits regular loading of tube-bundle reactors (with catalysts which contain, as active material, said catalytically active multielement oxide materials which contain at least one of the elements Nb and W and the elements Mo, V and, if required, C) having from 5 000 to 40 000 catalyst tubes which are such that, in the case of a random sample of 12 catalyst tubes, the difference between the arithmetic mean activity and the highest or lowest activity is not more than 8° C., frequently not more than 6° C., often not more than 4° C. and in advantageous cases not more than 2° C.

What is noteworthy about the novel process is that the above result is also achieved if all of the active material contained in the tube-bundle reactor was prepared in less than 100 or less than 75 or less than 50 batches of the thermal treatment of a precursor material. Frequently, the number of these batches is from 5 to 40.

The temperature which a salt bath (mixture of 53% by weight of potassium nitrate, 40% by weight of sodium nitrite and 11% by weight of sodium nitrate) flowing around the individual catalyst tube must have is used as a measure of the activity of the catalyst tube load so that, with a single pass of a reaction gas mixture comprising 4.8% by volume of acrolein, 7% by volume of oxygen, 10% by volume of steam and 78.2% by volume of nitrogen (at a space velocity of the catalyst load of 85 l(S.T.P.) of acrolein per l of catalyst load per hour) through the loaded catalyst tube, an acrolein conversion of 97 mol % is achieved (l of catalyst load does not include the volumes inside the catalyst tube where pure preliminary or subsequent beds of inert material are present but only the bed volumes which contained catalyst moldings (if necessary diluted with inert material)).

Loading of catalyst tubes in tube-bundle reactors, achievable in the manner described, is important particularly when the tube-bundle reactor is operated at an acrolein space velocity of the catalyst load which is ≧135 or ≧150 or ≧160 or ≧170 or ≧180 or ≧200 or ≧220 or ≧240 l(S.T.P.) per l per h. Of course, such a catalyst load is also advantageous in the case of lower acrolein space velocities.

As a rule, the acrolein space velocity of the catalyst load is, however, ≦350 or ≦300 or ≦250 l(S.T.P.) per l per h.

Otherwise, the tube-bundle reactor with the partial oxidation of acrolein to acrylic acid can be operated as described in DE-A 10307983, DE-A 19948523 and DE-A 19910508.

Finally, it should also be stated that the novel process permits in a simple manner residence times of ≧5 h or ≧10 h or ≧15 h or ≧20 h or ≧25 h for the precursor material to be thermally treated in the rotary tube furnace. As a rule, this residence time is ≦50 h.

Furthermore, it should be stated that the novel process is in particular also suitable for the preparation of multielement oxide active materials which contain the elements Mo, V, at least one of the two elements Te and Sb, and at least one of the elements from the group consisting of Nb, Pb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In in combination.

Frequently, the thermal treatment is carried out initially at from 150 to 350° C., preferably from 250 to 350° C., under an oxidizing (oxygen-containing) atmosphere (e.g. air) and then at from 350 to 1 000° C. or from 400 to 700° C. or from 400 to 650° C. in the absence of oxygen (e.g. under $N_2$). The thermal treatment under air can also be carried out continuously.

The combination preferably contains, from the final group of elements, the elements Nb, Ta, W and/or Ti, particularly preferably the element Nb.

The relevant multielement oxide active materials preferably contain the abovementioned element combination in the stoichiometry III

  (III), where $M^1$ is Te and/or Sb, $M^2$ is at least one of the elements from the group consisting of Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In, b is from 0.01 to 1, c is from >0 to 1 and d is >0 to 1.

Preferably, $M^1$ is Te and $M^2$ is Nb, Ta, W and/or Ti. $M^2$ is preferably Nb.

The stoichiometric coefficient b is advantageously from 0.1 to 0.6. In a corresponding manner, the preferred range for the stoichiometric coefficient c is from 0.01 to 1 or from 0.05 to 0.4 and advantageous values for d are from 0.01 to 1 or from 0.1 to 0.6.

It is particularly advantageous if the stoichiometric coefficients b, c and d are simultaneously in the abovementioned preferred ranges.

The abovementioned applies in particular when the active material consists of one of the abovementioned element combinations with regard to their elements other than oxygen.

In this case, these are in particular the multielement oxide active materials of the stoichiometry IV

  (IV), where the variables have the meaning stated with regard to stoichiometry III and n is a number which is determined by the valency and frequency of the elements other than oxygen in (IV).

Furthermore, the novel process is preferably suitable for the preparation of those multielement oxide active materials which either contain one of the above-mentioned element combinations or, with regard to the elements other than oxygen, consist of them and simultaneously have an X-ray diffraction pattern which exhibits reflections h and i whose peaks are at the diffraction angles (2Θ)) 22.2±0.5° (h) and 27.3±0.5° (i) (all data in this document which relate to an X-ray diffraction pattern are based on an X-ray diffraction pattern produced using CuKα radiation (Siemens diffractometer Theta-Theta D-5000, tube voltage: 40 kV, tube current: 40 mA, aperture V20 (variable), collimator V20 (variable), secondary monochromator aperture (0.1 mm), detector aperture (0.6 mm), measuring interval (2Θ): 0.02°, measuring time per step: 2.4 s, detector (scintillation counter))).

The full width at half height of these reflections may be very small or very pronounced.

The novel process is particularly suitable for the preparation of those of the abovementioned multielement oxide active materials whose X-ray diffraction pattern has, in addition to the reflections h, i, the reflection k whose peak is at 28.2±0.5° (k).

Preferred among the latter in turn for preparation according to the invention are those in which the reflection h is the one with the strongest intensity within the X-ray diffraction pattern and has a full width at half height of not more than 0.5°, and the novel process is very particularly preferably suitable for those for which the full widths at half height of the reflection i and of the reflection k are simultaneously ≦1° and the intensity $P_k$ of the reflection k and the intensity $P_i$ of the reflection i fulfill the relationship 0.2≦R≦0.85, better 0.3≦R≦0.85, preferably 0.4≦R≦0.85, particularly preferably 0.65≦R≦0.85, even more preferably 0.67≦R≦0.75 and very particularly preferably R=from 0.70 to 0.75 or R=0.72, where R is the intensity ratio defined by the formula $R=P_i/(P_i+P_k)$.

Preferably, the abovementioned X-ray diffraction patterns have no reflection whose maximum is at 2Θ=50±0.3°.

In this document, the definition of the intensity of a reflection in the X-ray diffraction pattern is based on the definition stated in DE-A 19835247 and DE-A 10122027 and that stated in DE-A 10051419 and DE-A 10046672. The same applies to the definition of the full width at half height.

In addition to the reflections h, i and k, the abovementioned X-ray diffraction patterns of multielement oxide active materials advantageously to be prepared according to the invention contain further reflections whose peaks are at the following diffraction angles (2Θ):

9.0±0.4° (l)

6.7±0.4° (o) and 7.9±0.4° (p).

It is furthermore advantageous if the X-ray diffraction pattern additionally contains a reflection whose peak is at the diffraction angle (2Θ)=45.2±0.4° (q).

Frequently, the X-ray diffraction pattern also contains the reflections 29.2±0.4° (m) and 35.4±0.4° (n).

It is furthermore advantageous if the element combinations defined in the formulae III and IV are present as pure i-phase. Since the catalytically active oxide material also contains k-phase, its X-ray diffraction pattern also contains, in addition to the abovementioned reflections, further reflections whose peaks are at the following diffraction angles (2Θ): 36.2±0.4° (m) and 50±0.4° (the terms i- and k-phase are used in this document as specified in DE-A 10122027 and DE-A 10119933).

If the reflection h is assigned the intensity 100, it is advantageous according to the invention if the reflections i, l, m, n, o, p and q have the following intensities on the same intensity scale:

i: from 5 to 95, frequently from 5 to 80, in some cases from 10 to 60;

l: from 1 to 30;

m: from 1 to 40;

n: from 1 to 40;

o: from 1 to 30;

p: from 1 to 30 and q: from 5 to 60.

If the X-ray diffraction pattern contains any of the abovementioned additional reflections, the full width at half height thereof is as a rule $\leq 1°$.

The specific surface area of multielement oxide active materials of the formula IV to be prepared according to the invention or of multielement oxide active materials which contain element combinations of the formula III is often from 1 to 30 m$^2$/g (BET surface area, nitrogen), especially when their X-ray diffraction pattern has the form described.

The preparation of the precursor materials of the multielement oxide active materials obtainable in the manner described appears in the prior art cited in connection with said materials. This includes in particular DE-A 10122027, DE-A 10119933, DE-A 10033121, EP-A 1192987, DE-A 10029338, JP-A 2000-143244, EP-A 962253, EP-A 895809, DE-A 19835247, WO 00/29105, WO 00/29106, EP-A 529853 and EP-A 608838 (in all embodiments of the two last-mentioned publications, spray drying is to be used as the drying method; for example, with an entry temperature of from 300 to 350° C. and an exit temperature of from 100 to 150° C.; countercurrent or cocurrent). The conditions of the thermal treatment of these precursor materials are likewise described in these publications.

The multielement oxide active materials described can be used as such (i.e. in powder form) or after shaping to suitable geometries (cf. for example the coated catalysts of DE-A 10051419 and the geometrical variants of DE-A 10122027) for the gas-phase catalytic partial oxidation and/or ammoxidation of lower hydrocarbons and lower organic compounds, such as propylene, propane and acrolein. They are suitable in particular for the preparation of acrolein and/or acrylic acid and for the preparation of acrylonitrile from propane and/or propene. The reaction conditions are likewise contained in the prior art cited.

The novel process also permits regular loading of tube-bundle reactors (with catalysts which comprise, as active materials, said catalytically active multielement oxide materials which contain the elements Mo, V, at least one of the two elements Te and Sb and at least one of the elements from the group consisting of Nb, Ta, etc. in combination) comprising from 5 000 to 40 000 catalyst tubes which are such that, for a random sample of 12 catalyst tubes, the difference between the arithmetic mean activity and the highest or lowest activity is not more than 8° C., frequently not more than 6° C., often not more than 4° C. and in advantageous cases not more than 2° C.

Noteworthy of the novel process is the fact that the above result is also achieved when all of the active material contained in the tube-bundle reactor was prepared in less than 100 or less than 75 or less than 50 batches of the thermal treatment of a precursor material. Frequently, the number of these batches is from 5 to 40.

The temperature which a salt bath (mixture of 53% by weight of potassium nitrate, 40% by weight of sodium nitrite and 7% by weight of sodium nitrate) flowing around the individual catalyst tube must have so that, during a single pass of a reaction gas mixture of 4.8% by volume of acrolein, 7% by volume of oxygen, 10% by volume of steam and 78.2% by volume of nitrogen (at a space velocity of the catalyst load of 85 l(S.T.P.) of acrolein per l of catalyst load per h) through the loaded catalyst tube, an acrolein conversion of 97 mol % is achieved is in turn used as a measure of the activity of the catalyst tube load (l of catalyst load does not include the volumes inside the catalyst tube where pure preliminary and subsequent beds of inert material are present, but only the bed volumes which contain the catalyst moldings (if necessary diluted with inert material)).

Such loading of catalyst tubes is important especially when the tube-bundle reactor is operated at an acrolein space velocity of the catalyst load which is $\geq 135$ or $\geq 150$ or $\geq 170$ or $\geq 200$ or $\geq 240$ l(S.T.P.) per l per h. As a rule, it is $\leq 350$ or $\leq 300$ or $\leq 250$ l(S.T.P.) per l per h.

WORKING EXAMPLE

A) Preparation of a Precursor Material for the Production of a Multielement Oxide Material of the Stoichiometry $Mo_{12}V_3W_{1.2}Cu_{2.4}O_x$ 16.3 kg of copper(II) acetate hydrate (content: 40.0% by weight of CuO) are dissolved in 274 l of water at 25° C. with stirring. A clear solution 1 was obtained.

Spatially separately therefrom, 614 l of water were heated to 40° C. and 73 kg of ammonium heptamolybdate tetrahydrate (81.5% by weight of $MoO_3$) were stirred in while maintaining at 40° C. Thereafter, heating was effected to 90° C. in the course of 30 minutes with stirring, and 11.3 kg of ammonium metavanadate and 10.7 kg of ammonium paratungstate heptahydrate (88.9% by weight of $WO_3$) were stirred in in succession and in the stated sequence while maintaining this temperature. A clear solution 2 was obtained.

The solution 2 was cooled to 80° C., and the solution 1 was then stirred into the solution 2. 130 l of a 25% strength by weight aqueous $NH_3$ solution which was at 25° C. was added to the mixture obtained. Stirring resulted in a clear solution, which briefly had a temperature of 65° C. and a pH of 8.5. A further 20 l of water at 25° C. were added to said solution. Thereafter, the temperature of the resulting solution increased again to 80° C. and said solution was then spray-dried using a spray dryer of the type S-50-N/R from Niro-Atomizer (Copenhagen) (gas inlet temperature: 350° C., gas outlet temperature: 110° C.). The spray-dried powder had a particle diameter of from 2 to 50 μm. 60 kg of spray-dried powder thus obtained were metered into a kneader of the type VM 160 (sigma blades) from AMK (Aachener Misch- und Knetmaschinen Fabrik) and kneaded with the addition of 5.5 l of acetic acid ($\approx$100% strength by weight, glacial acetic acid) and 5.2 l of water (screw speed: 20 rpm). After a kneading time of from 4 to 5 minutes, a further 6.5 l of water were added and the kneading process was continued until 30 minutes had elapsed (kneading temperature from about 40 to 50° C.). Thereafter, the kneaded material was emptied into an extruder and shaped by means of the extruder (from Bonnot Company (Ohio), type: G 103-10/D7A-572K (6" extruder W Packer)) to give extrudates (length: 1-10 cm; diameter: 6 mm). The extrudates were dried for 1 hour at 120° C. (material temperature) on a belt drive. The dried extrudates formed the precursor material to be thermally treated according to the novel process.

B) Preparation of the Catalytically Active Material by Novel Thermal Treatment in a Rotary Tube Furnace Apparatus The thermal treatment was carried out in a rotary tube furnace apparatus according to FIG. 1, with the dimensions and auxiliary elements according to the exemplary embodiment in the description of this document and under the following conditions:
- the thermal treatment was carried out batchwise with 300 kg of material which had been prepared as described in A);
- the angle of inclination of the rotary tube relative to the horizontal was ≈0°;
- the rotary tube rotated clockwise at 1.5 revolutions per minute;
- during the entire thermal treatment, a gas stream of 205 m$^3$(S.T.P.)/h was passed through the rotary tube, said gas stream (after displacement of the air originally contained) having the following composition and being supplemented at its exit from the rotary tube by a further 25 m$^3$(S.T.P.)/h of sealing nitrogen gas:
- 80 m$^3$(S.T.P.)/h composed of nitrogen base load (20) and gases liberated in the rotary tube
- m$^3$(S.T.P.)/h of sealing nitrogen gas (11),
- m$^3$(S.T.P.)/h of air (splitter (21)), and
- 70 m$^3$(S.T.P.)/h of recirculated gas (19).

The nitrogen sealing gas was fed in at 25° C. The mixture of the other gas streams, arriving from the heater, was fed into the rotary tube in each case at the temperature which the material in the rotary tube had in each case.
- the material temperature of 25° C. was increased substantially linearly to 300° C. in the course of 10 hours;
- the material temperature was then increased substantially linearly to 360° C. in the course of 2 hours;
- thereafter, the material temperature was reduced substantially linearly to 350° C. in the course of 7 hours;
- the material temperature was then increased substantially linearly to 420° C. in the course of 2 hours and this material temperature was maintained for 30 minutes;
- the 30 m$^3$(S.T.P.)/h of air in the gas stream passed through the rotary tube were then replaced by a corresponding increase in the nitrogen base load (with the result that the actual thermal treatment process was complete), the heating of the rotary tube was switched off and, by switching on the rapid cooling of the rotary tube by aspirating ambient air, the material was cooled to a temperature below 100° C. in the course of 2 hours and finally to ambient temperature; the gas stream was fed to the rotary tube at 25° C.;
- during the entire thermal treatment, the pressure (directly) downstream of the rotary tube exit of the gas stream was 0.2 mbar below the external pressure.

The oxygen content of the gas atmosphere in the rotary tube furnace was 2.99% by volume in all phases of the thermal treatment. The arithmetic mean of the ammonia concentration of the gas atmosphere in the rotary tube furnace over the total duration of the reductive thermal treatment was 4% by volume.

Figure 1:
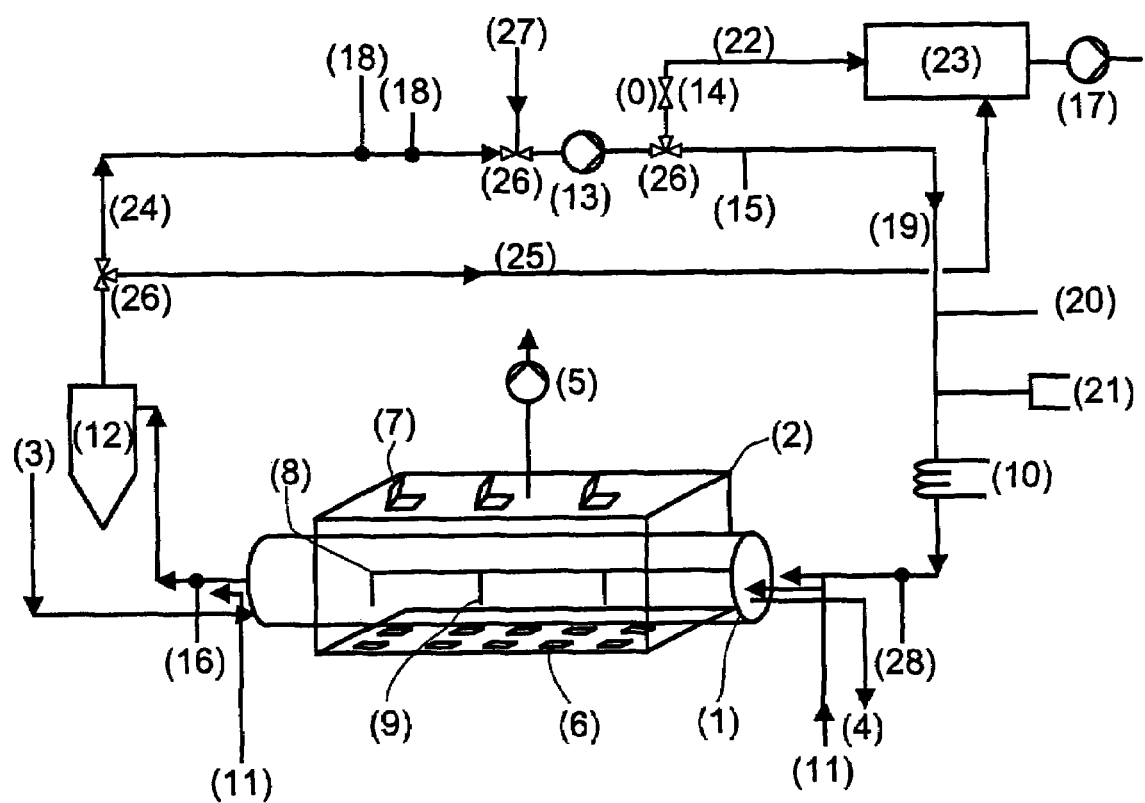
FIG. 1 shows a rotary tube furnace apparatus.
Figure 2:
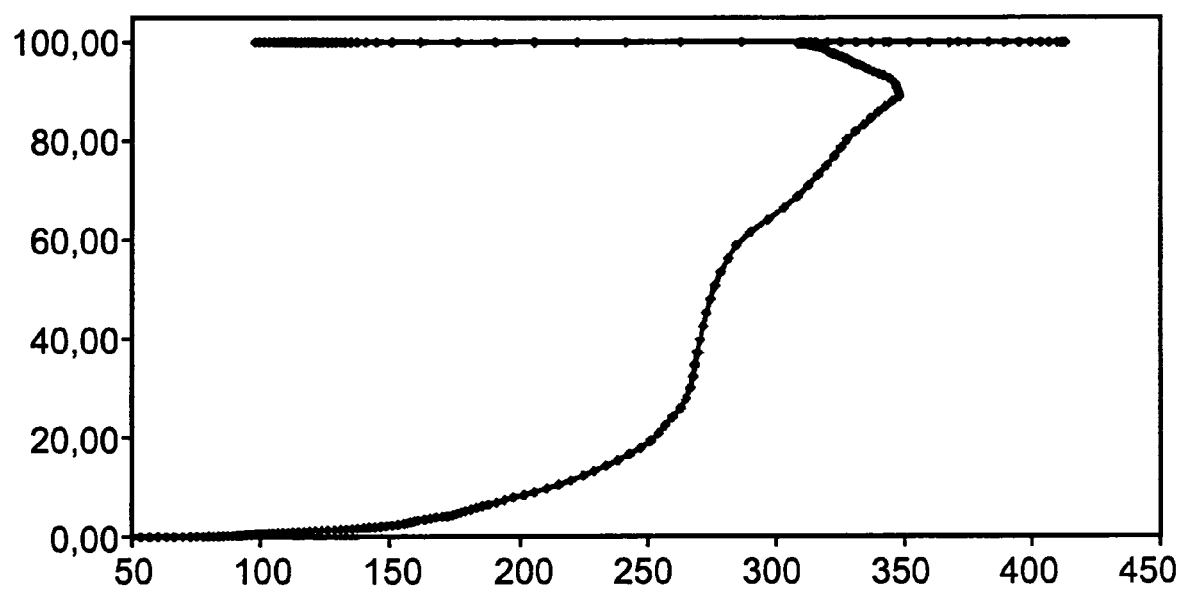
FIG. 2 shows the amount of ammonia liberated as a function of the material temperature in ° C. from the precursor material as a percentage of the total amount of ammonia liberated from the precursor material in the entire course of the thermal treatment.
Figure 3:
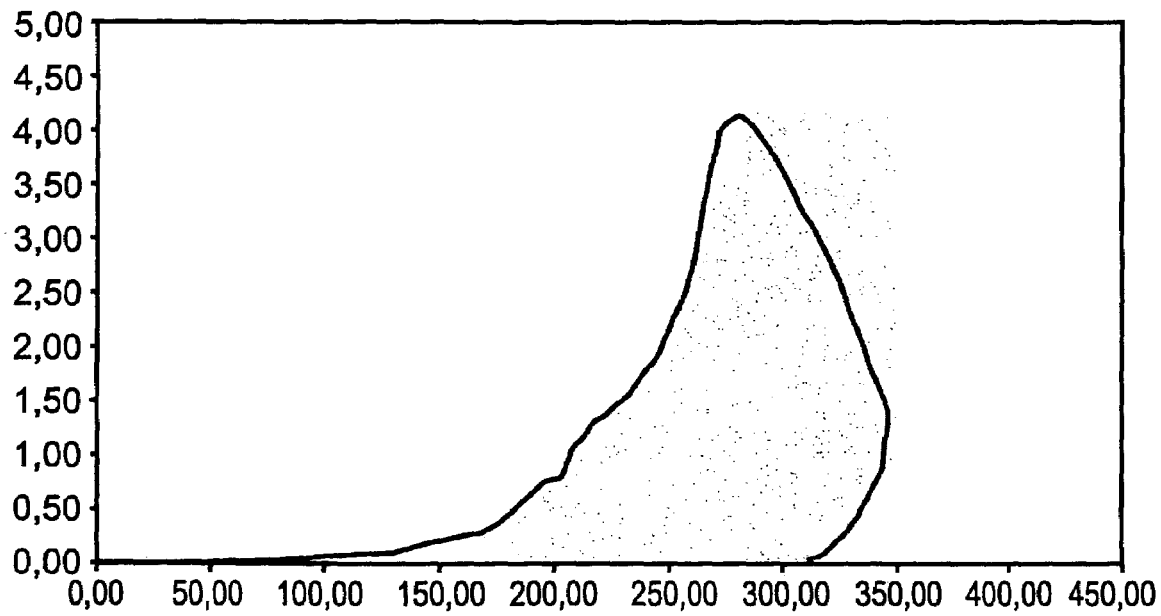
FIG. 3 shows the ammonia concentration of the atmosphere, in % by volume, in which the thermal treatment was carried out as a function of the material temperature, in ° C., during the thermal treatment.
Figure 4:
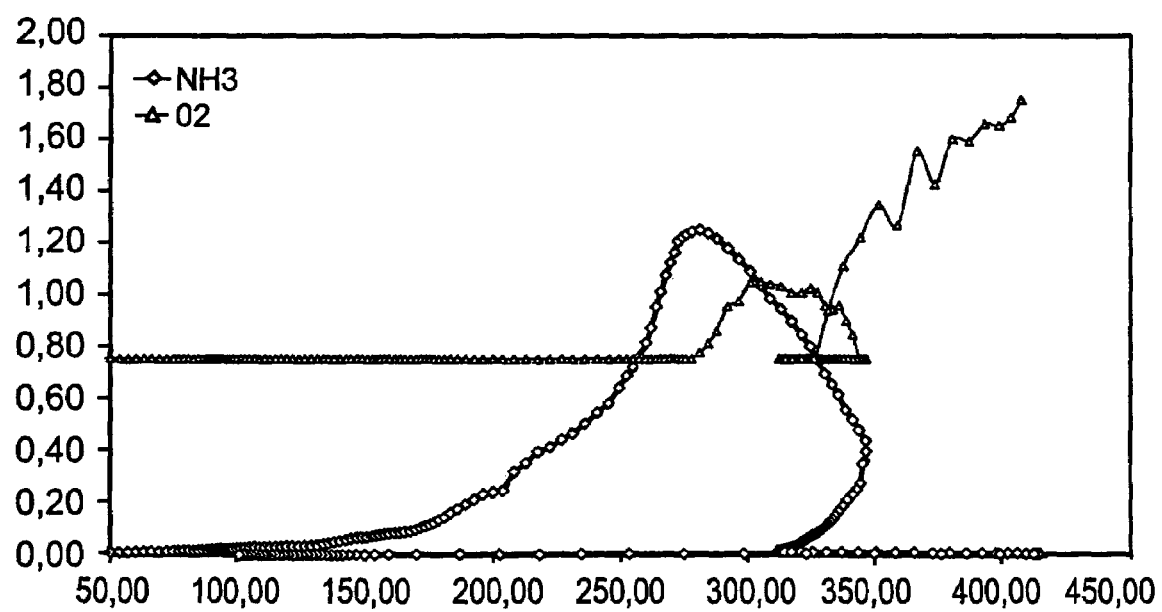
FIG. 4 shows, as a function of the material temperature, the molar amounts of molecular oxygen and of ammonia which were fed per kg of precursor material per hour over the thermal treatment with the gas stream into the rotary tube.

C) Shaping of the Multimetal Oxide Active Material

The catalytically active material obtained under B) was milled by means of a biplex cross-flow calcifying mill (BO 500) (from Hosokawa-Alpine Augsburg) to give a finely divided powder, 50% of the particles of which passed through a sieve of mesh size from 1 to 10 μm and whose particle fraction with a longest dimension above 50 μm was less than 1%.

Annular supports (7 mm external diameter, 3 mm length, 4 mm internal diameter, steatite C220 from CeramTec having a surface roughness R$_z$ of 45 μm) were coated by means of the milled powder as in Si of EP-B 714700. The binder was an aqueous solution of 75% by weight of water and 25% by weight of glycerol.

However, in contrast to the abovementioned example S1, the proportion of active material of the resulting coated catalysts was chosen to be 20% by weight (based on the total weight of support and active material). The ratio of powder and binder was adjusted to be proportional.

D) Testing of the Coated Catalysts

The coated catalysts were tested as follows in a model catalyst tube around which a salt bath (mixture of 53% by weight of potassium nitrate, 40% by weight of sodium nitrite and 7% by weight of sodium nitrate) flowed:
Model catalyst tube: V2A stainless steel, 2 mm wall thickness, 26 mm internal diameter, centered thermal sleeve (for receiving a thermocouple) of external diameter 4 mm, 1.56 l of the free space of the model catalyst tube were filled with the coated catalyst.

The reaction gas mixture had the following starting composition:

4.8% by volume of acrolein, 7% by volume of oxygen, 10% by volume of steam, 78.2% by volume of nitrogen.

The model catalyst tube was loaded with 2 800 l (S.T.P.)/h of reaction gas starting mixture. This corresponds to a loading of the catalyst load of 86 l (S.T.P.) per l per h. The temperature of the salt bath was adjusted so that an acrolein conversion of 97 mol % resulted during a single pass.

12 model catalyst tubes loaded in the manner described were compared with one another in each case in ten experiments independently of one another.

In all cases, the salt bath temperature necessary for the required acrolein conversion was within the interval 257±4° C. The selectivity of the acrylic acid formation in all cases was about 94.8 mol %.

Working Example 2

Everything was carried out as in working example 1. However, the shaping of the multimetal oxide active material was effected as follows:

70 kg of annular supports (7.1 mm external diameter, 3.2 mm length, 4.0 mm internal diameter; steatite of type C220 from CeramTec, having a surface roughness $R_z$, of 45 µm and a total pore volume of ≦1% by volume, based on the volume of the support) were introduced into a coating pan (angle of inclination 90°; Hicoater from Lödige, Germany) having an internal volume of 200 l. The coating pan was then caused to rotate at 16 rpm. From 3.8 to 4.2 liters of an aqueous solution of 75% by weight of water and 25% by weight of glycerol were then sprayed onto the supports via a nozzle in the course of 25 minutes. At the same time, in the same period, 18.1 kg of the milled multimetal oxide active material (the specific surface area was 13.8 m²/g) were metered in continuously via a vibrating channel outside the spray cone of the atomizer nozzle. During the coating, the powder fed in was completely taken up onto the surface of the supports, and agglomeration of the finely divided oxidic active material was not observed. After the end of the addition of active material powder and water, hot air at 100° C. (alternatively from 80 to 120° C.) (about 400 m³/h) was blown into the coating pan at a rotational speed of 2 rpm for 40 minutes (alternatively from 15 to 60 minutes).

Annular coated catalysts whose proportion of oxidic active material was 20% by weight, based on the total mass, were obtained. The coat thickness, considered both over the surface of one support and over the surface of different supports, was 170±50 µm.

The coated catalysts were tested as in working example 1. The results obtained corresponded to the results obtained in working example 1.

Figure 5:
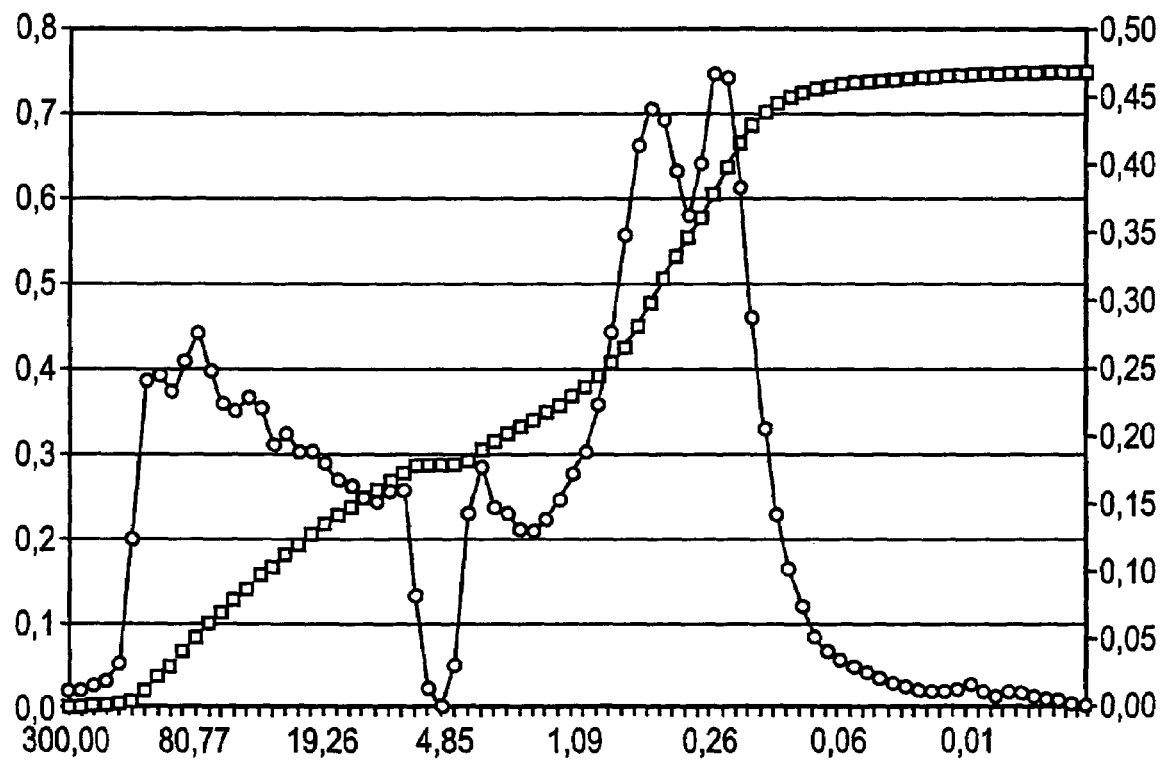
FIG. 5 shows the pore distribution of the milled active material powder before its shaping—this is the active metal powder of Working Example 2.

FIG. 5 also shows the pore distribution of the milled active material powder before its shaping. The pore diameter in µm is plotted along the abscissa (logarithmic scale).

The logarithm of the differential contribution, in ml/g, of the respective pore diameter to the total pore volume is plotted along the right ordinate (curve O). The maximum has the pore diameter with the greatest contribution to the total pore volume. The integral over the individual contributions of the individual pore diameters to the total pore volume is plotted in ml/g along the left ordinate (curve □). The endpoint is the total pore volume (all data in this document regarding the determinations of total pore volumes and of diameter distributions over these total pore volumes are based, unless stated otherwise, on determinations by the mercury porosimetry method using the Auto Pore 9220 apparatus from Micromeritics GmbH, 4040 Neuβ, Germany (bandwidth 30 Å to 0.3 mm); all data in this document regarding determination of the specific surface areas or of micro pore volumes are based on determinations according to DIN 66131 (determination of the specific surface area of solids by gas adsorption ($N_2$) according to Brunauer-Emmet-Teller (BET))).

Figure 6:
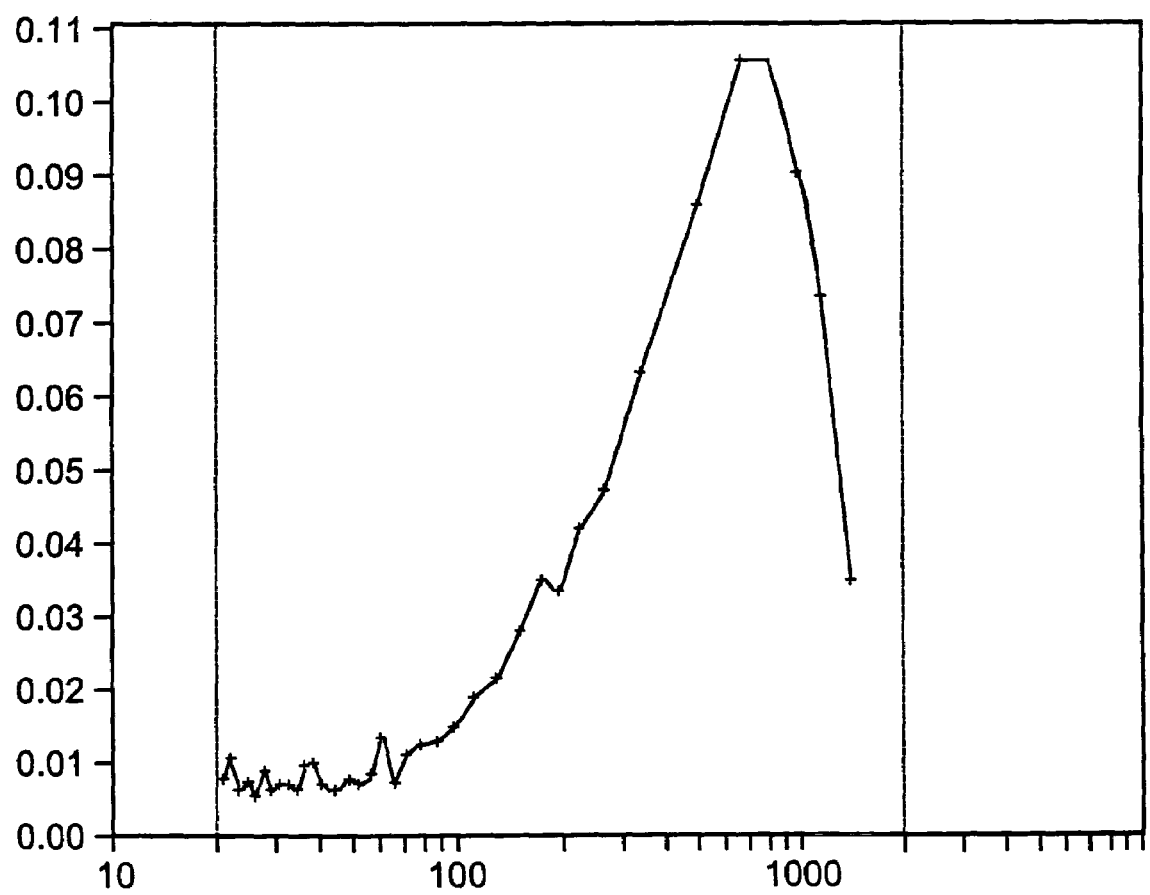
FIG. 6 shows the individual contributions of the individual pore diameters (abscissa, in Angstrom, logarithmic scale) in the micropore range to the total pore volume for the active material powder before its shaping, in ml/g (ordinate) and concerns the active material powder of Working Example 2.

FIG. 6 shows the individual contributions of the individual pore diameters (abscissa, in Ångström, logarithmic scale) in the micropore range to the total pore volume for the active material powder before its shaping, in ml/g (ordinate).

Figure 7:
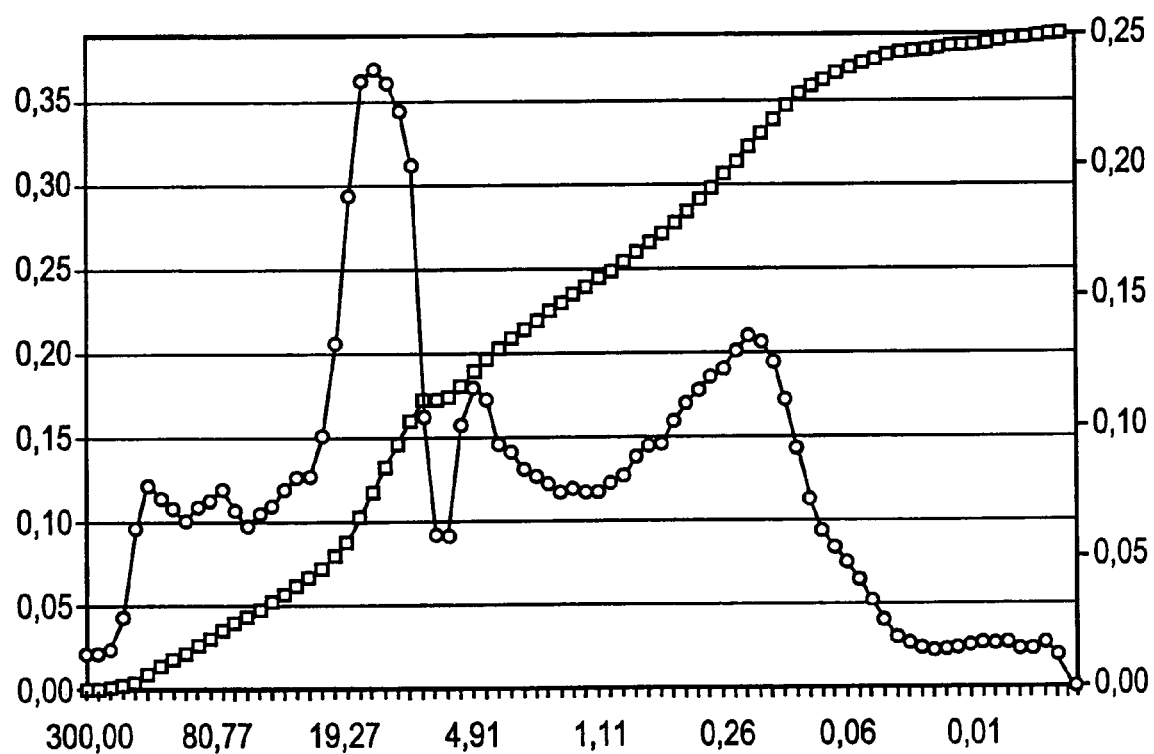
FIG. 7 shows the same as FIG. 5 but for multimetal oxide active material subsequently detached from the annular coated catalyst by scratching off mechanically.

FIG. 7 shows the same as FIG. 5 but for multimetal oxide active material (the specific surface area was 12.9 m²/g) subsequently detached from the annular coated catalyst by scratching off mechanically.

Figure 8:
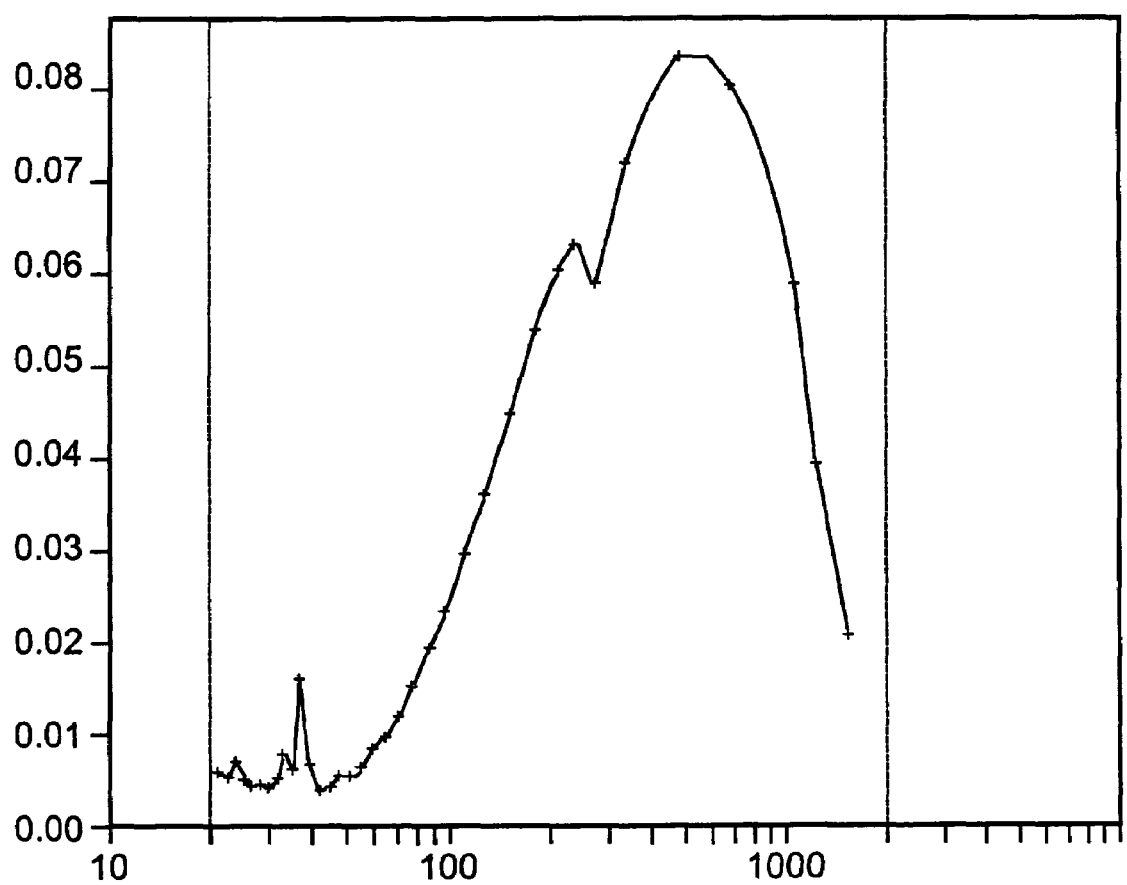
FIG. 8 shows the same as FIG. 6 but for multimetal oxide active material subsequently detached from the annular coated catalyst by scratching off mechanically.

FIG. 8 shows the same as FIG. 6 but for multimetal oxide active material subsequently detached from the annular coated catalyst by scratching off mechanically.

Working Example 3

Everything was carried out as in working example 1. However, the shaping of the multimetal oxide active material was effected as follows:

70 kg of spherical supports (diameter from 4 to 5 mm; steatite of type C220 from CeramTec, having a surface roughness $R_z$, of 45 µm and a total pore volume of ≦1% by volume, based on the volume of the support) were introduced into a coating pan (angle of inclination 90°; Hicoater from Lödige, Germany) having an internal volume of 200 l. The coating pan was then caused to rotate at 16 rpm. From 2.8 to 3.3 liters of water were sprayed onto the supports via a nozzle in the course of 25 minutes. At the same time, in the same period, 14.8 kg of the milled multimetal oxide active material were continuously metered in via a vibrating channel outside the spray cone of the atomizer nozzle. During the coating, the powder fed in was completely taken up onto the surface of the supports, and agglomeration of the finely divided oxidic active material was not observed. After the end of the addition of powder and water, hot air at 100° C. (alternatively from 80 to 120° C.) (about 400 m³/h) was blown into the coating pan at a rotational speed of 2 rpm for 40 minutes (alternatively from 15 to 60 minutes). Spherical coated catalysts whose proportion of oxidic active material was 17% by weight, based on the total mass, were obtained. The coat thickness, considered both over the surface of one support and over the surface of different supports, was 160±50 µm.

Figure 9:
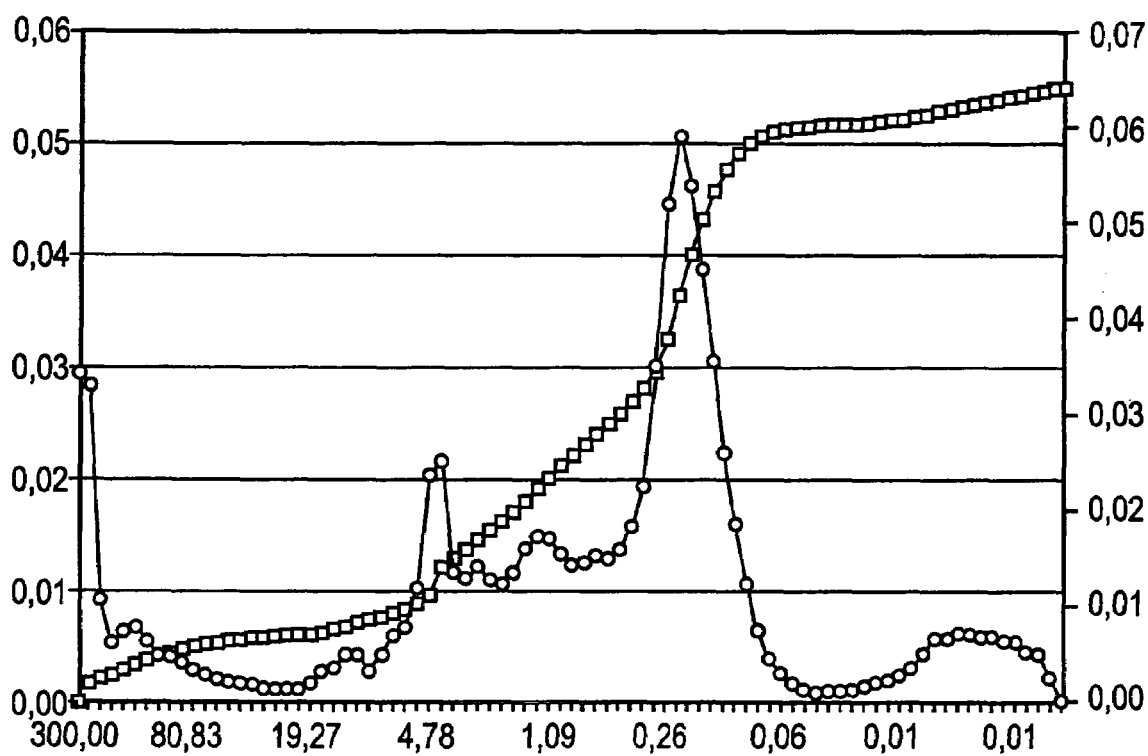
FIG. 9 shows the analog of FIG. 7 but for the multimetal oxide active material of Working Example 3.

FIG. 9 shows the analog of FIG. 7 (the specific surface area of the scratched-off multimetal oxide active material was 15 m²/g).

Figure 10:
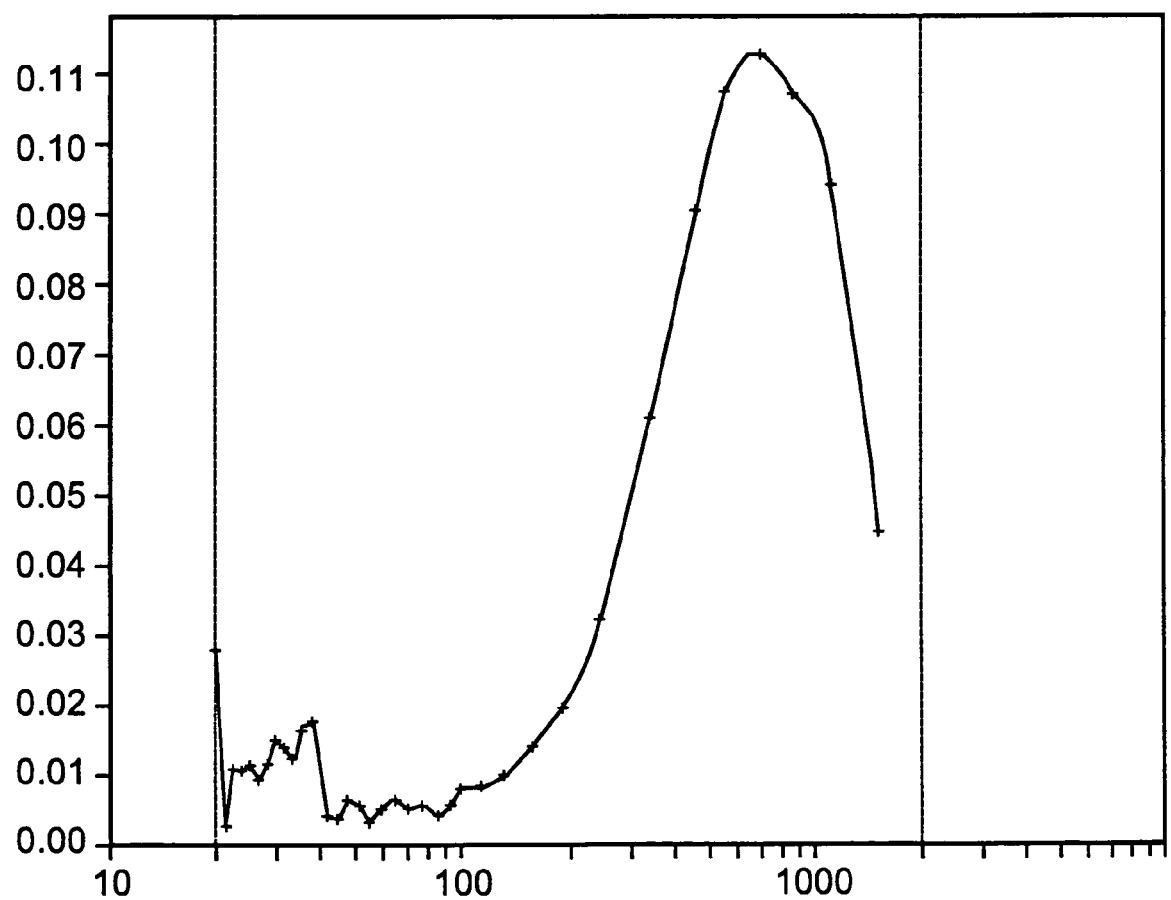
FIG. 10 shows the analog of FIG. 8 but for the multimetal oxide active material of working example 3.

FIG. 10 shows the analog of FIG. 8.

The spherical coated catalyst was tested as described in preparation example 1 for the annular coated catalyst.

All coated catalysts prepared by way of example in this document are particularly suitable for acrolein partial oxidations at high acrolein space velocities of the catalyst load (e.g. from ≧135 to 350 l (S.T.P.) per l per h).

We claim:

1. A process for the thermal treatment of a precursor material of a catalytically active multi-element oxide material, comprising thermally treating the precursor material in a rotary tube furnace through which a gas stream flows at a material temperature of from 300° C. to 450° C. to form the catalytically active multi-element oxide material, wherein the catalytically active multi-element oxide material comprises the elements Mo, V, and at least one of the elements Nb and W, wherein the molar fraction of the element Mo in the catalytically active multi-element material, based on the total amount of all elements other than oxygen in the catalytically active multi-element oxide material, ranges from 20 mol % to 80 mol %, wherein the molar ratio of Mo to V in the catalytically active multi-element oxide material, Mo/V, ranges from 15:1 to 1:1, wherein the molar ratio Mo/(W and Nb) ranges from 80:1 to 1:4, wherein the precursor material is obtained by a process comprising preparing an intimate dry blend comprising ammonium ions from starting compounds, wherein the starting compounds comprise the elemental constituents of the multi-element oxide material other than the oxygen, wherein the gas in the gas stream comprises from 0.5% to 4% by volume of $O_2$ at every point in time during the thermally treating, from 1% to 8% by volume of $NH_3$, averaged over the total duration of thermally treating, and steam and/or inert gas in residual amounts, wherein the $NH_3$ content in the gas stream during the thermally treating passes through a maximum that is below 20% by volume, wherein at least a portion of the gas stream flowing through the rotary tube furnace is circulated, and wherein no additional amount of $NH_3$ is added to the gas stream during the thermal treatment process.

2. The process as claimed in claim 1, wherein the pressure in the rotary tube furnace is below the ambient pressure.

3. The process claimed in claim 1, wherein the gas stream in the rotary tube comprises at least one of $CO_2$, acetic acid, $NO_x$, $NH_3$, CO, $SO_2$ and acetonitrile.

4. The process as claimed in claim 1, wherein the circulated portion of the gas stream flowing through the rotary tube furnace is fed via a cyclone.

5. The process as claimed in claim 1, wherein the temperature of the treated precursor material at the end of the thermal treatment is reduced by at least 300° C. in the course of a period of $\geq 0.5$ h and $\leq 5$ h.

6. The process as claimed in claim 1, wherein, for regulating the total amount of gas stream fed to the rotary tube, the principle of mass flow rate measurement based on Coriolis forces, the principle of aperture plate measurement based on pressure differences or the principle of thermal convection is used.

7. The process as claimed in claim 1, which is carried out in a rotary tube furnace apparatus which comprises: a) at least one recycle gas compressor; b) at least one exit gas compressor; c) at least one pressure reducer; d) at least one fresh gas feed; e) at least one heatable rotary tube and f) at least one recycle gas pipe.

8. The process as claimed in claim 7, wherein the rotary tube furnace apparatus additionally comprises at least one control valve.

9. The process as claimed in claim 7, wherein the rotary tube furnace apparatus additionally comprises at least one cyclone.

10. The process as claimed in claim 7, wherein the rotary tube furnace apparatus additionally comprises an apparatus for rapid cooling, which comprises an envelope which surrounds the rotary tube and has, on one side, orifices through which ambient air is aspirated by means of a fan and can be discharged through flaps present on the opposite side of the envelope and having an adjustable orifice.

11. The process as claimed in claim 1, wherein the residence time of the precursor material in the rotary tube furnace is $\geq 5$ h.

* * * * *